United States Patent
Grof

(10) Patent No.: US 10,539,521 B2
(45) Date of Patent: Jan. 21, 2020

(54) SYSTEM AND METHOD FOR READING X-RAY-FLUORESCENCE MARKING

(71) Applicants: SOREQ NUCLEAR RESEARCH CENTER, Yavne (IL); SECURITY MATTERS LTD., Kibbutz Ketura (IL)

(72) Inventor: Yair Grof, Rehovot (IL)

(73) Assignees: SOREQ NUCLEAR RESEARCH CENTER, Yavne (IL); SECURITY MATTERS LTD., Kibbutz Ketura (IL)

( * ) Notice: Subject to any disclaimer, the term of this patent is extended or adjusted under 35 U.S.C. 154(b) by 104 days.

(21) Appl. No.: 15/563,756

(22) PCT Filed: Mar. 31, 2016

(86) PCT No.: PCT/IL2016/050340
§ 371 (c)(1),
(2) Date: Oct. 2, 2017

(87) PCT Pub. No.: WO2016/157185
PCT Pub. Date: Oct. 6, 2016

(65) Prior Publication Data
US 2018/0095045 A1  Apr. 5, 2018

Related U.S. Application Data

(60) Provisional application No. 62/142,100, filed on Apr. 2, 2015.

(51) Int. Cl.
*G01N 23/223* (2006.01)
*G01N 33/42* (2006.01)
*G01N 23/2202* (2018.01)

(52) U.S. Cl.
CPC ....... *G01N 23/223* (2013.01); *G01N 23/2202* (2013.01); *G01N 33/42* (2013.01); *G01N 2223/076* (2013.01); *G01N 2223/652* (2013.01)

(58) Field of Classification Search
CPC .. G01N 23/223; G01N 23/2202; G01N 33/42; G01N 2223/076; G01N 2223/652
(Continued)

(56) References Cited

U.S. PATENT DOCUMENTS 6,418,193 B1 * 7/2002 Albagli ............... A61B 6/4035
348/E5.086
8,158,432 B2 4/2012 Grof et al.
(Continued)

FOREIGN PATENT DOCUMENTS

CN  203824940  *  9/2014
GB  2062221  5/1981
(Continued)

OTHER PUBLICATIONS

Author: Chaleampong Kongcharoen et al., Title: Autoregressive Integrated Moving Average with Explanatory Variable (ARIMAX) Model for Thailand Export, Date: Jun. 23, 2013 (Year: 2013).*
(Continued)

*Primary Examiner* — Taeho Jo
(74) *Attorney, Agent, or Firm* — Browdy and Neimark, P.L.L.C.

(57) ABSTRACT

In a method and a system for authenticating an object marked with XRF marking, a wavelength spectral profile is provided of a detected portion of an X-Ray signal arriving from an object in response to X-Ray or Gamma-Ray radiation applied to the object and the wavelength spectral profile is filtered to suppress trend and periodic components from the wavelength spectral profile to obtain a filtered profile with improved signal to noise or signal to clutter ratio. The object can be authenticated by processing the filtered profile and identifying one or more peaks therein, which satisfy a
(Continued)

predetermined condition, whereby the wavelengths of the identified peaks are indicative of the signatures of materials included in the object.

22 Claims, 10 Drawing Sheets

(58) Field of Classification Search
USPC .................................................. 378/44
See application file for complete search history.

(56) References Cited

U.S. PATENT DOCUMENTS

| | | | |
|---|---|---|---|
| 8,275,193 B2* | 9/2012 | Lin | G06K 9/3216 |
| | | | 382/103 |
| 8,590,800 B2 | 11/2013 | Baque | |
| 8,864,038 B2 | 10/2014 | Marka et al. | |
| 2003/0194053 A1* | 10/2003 | Schramm | G01N 23/223 |
| | | | 378/45 |
| 2006/0013360 A1* | 1/2006 | Sommer, Jr. | B07C 5/3427 |
| | | | 378/44 |
| 2006/0039530 A1* | 2/2006 | Kenning | G01N 23/223 |
| | | | 378/44 |
| 2006/0086901 A1* | 4/2006 | Price | G01N 21/31 |
| | | | 356/63 |
| 2006/0239401 A1* | 10/2006 | Sommer, Jr. | B07C 5/3427 |
| | | | 378/44 |
| 2007/0189449 A1* | 8/2007 | Baumann | A61B 6/484 |
| | | | 378/44 |
| 2008/0061234 A1* | 3/2008 | Nakamura | G01N 23/2252 |
| | | | 250/310 |
| 2008/0095309 A1* | 4/2008 | Puusaari | G01N 23/223 |
| | | | 378/44 |
| 2008/0226025 A1* | 9/2008 | Harding | G01N 23/223 |
| | | | 378/44 |
| 2009/0141961 A1* | 6/2009 | Smith | G06K 9/00577 |
| | | | 382/135 |
| 2009/0195776 A1* | 8/2009 | Durst | G01J 3/02 |
| | | | 356/326 |
| 2010/0295689 A1* | 11/2010 | Armistead, Jr. | G06K 9/00 |
| | | | 340/600 |
| 2012/0093286 A1* | 4/2012 | Peterson | G01N 23/223 |
| | | | 378/45 |
| 2012/0286046 A1* | 11/2012 | Ciurczak | G01J 3/0262 |
| | | | 235/454 |
| 2012/0307962 A1* | 12/2012 | Cho | A61K 49/0065 |
| | | | 378/6 |
| 2013/0299591 A1 | 11/2013 | Marka et al. | |
| 2014/0072095 A1* | 3/2014 | Feser | G01N 23/2206 |
| | | | 378/4 |
| 2015/0253263 A1* | 9/2015 | Feser | G01N 23/2206 |
| | | | 378/6 |

FOREIGN PATENT DOCUMENTS

| | | |
|---|---|---|
| JP | 11-316199 A | 11/1999 |
| KR | 101273746 | 6/2013 |

OTHER PUBLICATIONS

Author: G. H. Asbury et al., Title: X-ray Fluorescence Spectroscopy Method Development for Quantitative Evaluation of Carpet Cleaning Technology, Date: Mar./Apr. 2011 (Year: 2011).*
Cantalejo, et al., Climate forcing of fine-grained deep-marine systems in an active tectonic setting: Middle Eocene, Ainsa Basin, Spanish Pyrenees, Palaeogeography, Palaeoclimatology, Palaeoecology, Jun. 2014, pp. 351-371, vol. 410.
Couture, Rex, Background Subtraction for Trace-Element Analysis-Analytical Comparison of Methods, Advances in X-ray Analysis, 2002, pp. 441-446, vol. 45.
McIntyre, et al., X-Ray fluorescence spectroscopy and mapping using excitation from white and broad bandpass synchrotron radiation, Journal of Analytical Atomic Spectrometry, Jun. 2010, pp. 1381-1389, vol. 25.

* cited by examiner

SYSTEM AND METHOD FOR READING X-RAY-FLUORESCENCE MARKING

TECHNOLOGICAL FIELD

The present invention is in the field of X-Ray-Fluorescence (XRF) marking and particularly relates to techniques for reading XRF signals indicative of materials and compositions used for marking objects.

BACKGROUND

X-ray fluorescence (XRF) marking is a technique used to detect and possibly quantify chemical material elements and/or composition constituents which can serve for marking an object. The parameters/identity of an object can then be identified based on the detected materials.

In the following, X-ray fluorescence (XRF) is used to refer to the emission of characteristic "secondary" (or fluorescent) X-rays from a material that has been excited by primary X-rays or gamma rays radiation. The term fluorescence refers to absorption of radiation of a specific energy resulting in the re-emission of radiation of a different energy (typically lower). The X-ray fluorescence (XRF) phenomenon is based on the fact that when materials are exposed to short-wavelength X-rays or gamma rays, they may expel electrons from inner orbitals of the atom, which thus cause electrons in higher orbitals to "fall" into the lower/inner orbital, and, in the process, release photons with energy equal to the energy difference between the two orbitals involved. Different chemical elements have electronic orbitals/shells of different characteristic energies, and therefore the spectral profile of an XRF response from an object/material is indicative of the chemical elements and possibly of the amount of each element included in the material/object.

Counterfeiting and supply chain diversion of materials are phenomena that impact many fields. Many materials of inferior quality, including but not limited to raw materials, electronics, polymers and pharmaceuticals are counterfeited by unscrupulous manufacturers and enter the supply chain, often by copying labeling associated with "brand" companies. To this end there are various techniques known in the art which utilize XRF marking to identify object/materials and determine their source/manufacturer/owner and/or various parameter, thereby enabling to discern between the original materials/goods and counterfeit materials/goods. Since chemical makeup of the original and counterfeited materials may be similar, some techniques utilize additive XRF markers (such as compositions of materials having a specific a-priori known XRF signature), which are specifically added to the object to enable identification of the object and/or certain parameters thereof, such as its source.

For example U.S. Pat. No. 8,590,800 discloses a method of authenticating and/or identifying an article containing a chemical marking agent, which is substantially inseparably enclosed in a marker as a carrier and contains selected chemical elements and/or compounds in the form of marker elements, in concentrations based on a predetermined encryption code, which method comprises the steps of: i) qualitatively and/or quantitatively identifying the marker elements of the chemical marking agent, and ii) comparing the values identified in step (i) with the predetermined encryption code.

U.S. Pat. No. 8,864,038 discloses a material tracing technique for encoding information in a material. The technique includes storing information to be encoded in the material, generating a number based on the information, determining an amount of at least one tracer to be incorporated into the material corresponding to the number, and incorporating the determined amount of the at least one tracer into the material. Decoding information encoded in the material includes measuring an amount of the at least one tracer, in some embodiments after tracer activation, determining a number corresponding to the measured at least one tracer, and decoding the number to obtain information associated with the material.

U.S. Pat. No. 8,158,432 discloses a system for marking a fluid by a marker, the fluid flowing from a source to a destination, the system including a sensor for determining a value of a fluid property and a fluid flow controller for admitting a selected amount of the marker to the fluid, wherein the selected amount is determined according to the fluid value and a predetermined concentration of the marker in the fluid in the destination.

GENERAL DESCRIPTION

Solid waste, in many countries, must be disposed of in facilities designed for disposal of such waste, such as landfills. Solid waste may comprise construction waste, which is waste that results from destruction or renovation of roads, buildings and other man-made structures. Construction waste may comprise concrete, asphalt, metal, wood, insulation materials, drywall, glass, plastic and other associated debris.

In many countries, disposal of solid waste is associated with high costs stemming from transportation costs, to ship the waste to an appropriate disposal facility, and disposal costs, collected by the disposal facility to process the waste. Although contractors responsible for private and municipal construction are frequently required to dispose of construction waste and bear the costs of such disposal, unscrupulous contractors occasionally dispose of waste in illegal dumping grounds in order to avoid disposal costs. Illegal dumping has negative environmental and aesthetic consequences. As a result, authorities often criminalize illegal dumping and levy high fines from violators who are found to illegally dump solid waste. Usually, authorities are only able to prosecute offenders who are witnessed "red-handed" while illegally dumping. Enforcement of laws associated with illegal dumping is difficult because enforcement officials are frequently not present at the times and places where citizens illegally dump waste. There remains a difficulty in associating solid waste found in areas in which dumping is prohibited, with the perpetrator of illegal dumping.

There is therefore a need in the art for a marking technique suitable for use in marking and identification of objects/materials, such as solid waste in a manner allowing in-situ detection of the marker signature marking the objects/materials, in the place at which they are located (e.g. in the field outdoors, without carrying a sample of the object to be examined to a specialized lab).

However, reliable and accurate identification of XRF markers by conventional X-ray fluorescence (XRF) marking techniques requires obtaining XRF signals with relatively high signal to noise ratio (SNR) and/or with relatively high signal to clutter ratio (SCR) which may often not be available when attempting to measure XRF signals in-situ, in field conditions, by utilizing portable XRF detection/measurement devices. This is due to several reasons, among them being:

Since this XRF signal is a secondary fluorescence signal (relatively weak), high power X-ray/Gamma-ray radiation emitters may be required to obtain the XRF signal with SNR/SCR sufficient for use with conventional techniques, while such high power X-ray/Gamma-ray radiation emitters may not be available and/or may not be suitable for use outdoors and/or with portable devices without proper protection;

When operating in-situ and without vacuum conditions, the XRF signal from the examined object may suffer significant attenuation when it passes through the air between the examined object and the detector, thus impairing the SNR of the measurement;

Back scattering of primary radiation from the examined object and/or objects in its vicinity, as well as interfering signals from neighboring peaks and/or unwanted XRF response from contaminating materials/objects (e.g. other foreign/waste materials) located in the vicinity (e.g. at/on) the examined objects may produce significant clutter, deteriorating the SCR of the measurement;

Size and weight limitation of a portable XRF system may restrict use of accurate X-Ray detectors/spectrometers, and might permit use of relatively small and light X-Ray detectors/spectrometers associated with higher internal noise (e.g. electronic/instrumental noise of the detection device) and/or low spectral resolution affecting the SNR of the measurement;

Thus for some or all of the above reasons, and possibly also for other reasons, current techniques for reading XRF marking reliably and accurately are typically performed in controlled environments (e.g. laboratories and/or other suitable facilities/systems).

The present invention provides a novel technique for reading XRF markings of objects (e.g. solid-materials but not only) with improved accuracy and reliably. The technique of the invention facilitates use of handheld/portable XRF readers for reading XRF markings of objects in un-controlled environments (e.g. in-situ, where the object to be examined is found/located). More specifically, certain embodiments of the present invention provide a novel XRF signal processor and XRF signal processing method allowing to extract an accurate XRF signature (i.e. hereinafter also indicated as fingerprint) of the examined object, even from a relatively noisy signal of deteriorated SNR and/or SCR obtained from handheld/portable XRF readers which may be operated in an un-controlled environment.

Certain aspects of the XRF signal processing technique of the invention are based on the inventors' understanding that much of the noise and clutter appearing in a noisy XRF signal appear in the form of a trend and/or periodic components appearing in the wavelength spectrum profile of the signal, and that application of proper filtration to remove such components may yield a filtered spectral profile at which the XRF signature appears with significantly higher SNR/SCR. To this end, certain embodiments of the present invention provide a novel XRF signal processor and XRF signal processing method, which utilize time series processing methods, such as Auto-Regressive (AR) and Moving Average (MA) techniques to filter the spectral profile of the XRF signal. As will be appreciated from the description below, the present invention also provides specific AR models and/or MA models, such as and Auto Regressive Integrated Moving Average (ARIMA) model specifically designed for filtering XRF signals. Also certain embodiments provide methods, based on the Box-Jenkins and/or Seasonal-Decomposition approaches for applying the Auto Regressive models and/or Moving Average models to filter the wavelength spectra of an XRF signal. Indeed AR and MA models, such as ARIMA, as well as Box-Jenkins and Seasonal-Decomposition, are generally time series analysis statistical techniques which are conventionally used for analyzing time series data typically consisting of successive measurements made over a time interval. Yet, surprisingly the inventors of the present invention have found that application of these techniques (e.g. with proper adjustments often arrived at via trial and error), to filtration of the wavelength spectrum of XRF, all provide comprehensive results in filtering out noise and/or clutter from XRF signals.

It should be noted that here and in the following, the phrase uncontrolled environment should be understood as any environment such as outdoors, where the XRF signal propagates to the detector through the ambient media/air without vacuum conditions and where contaminating objects/material which may reside near/on the examined material are not necessarily removed away before the examination. It should also be noted that the terms handheld and portable when used herein in the context of the XRF device indicate a device that can be configured to be carried by personnel and which is operable in situ to perform the XRF reading.

Thus in certain embodiments the XRF signal processor and/or XRF signal processing method of the present invention are used to accurately extract XRF signatures from a noisy XRF signal. As indicated above, the processing method/system of the invention may be used for processing XRF signals obtained by handheld/portable XRF readers. Accordingly, certain aspects of the present invention are directed to a novel XRF device incorporating the XRF signal processor and/or XRF signal processing method of the present invention. Certain embodiments of the present invention also provide a novel handheld/portable XRF device configured to include the XRF signal processor of the invention and/or to be in communication with the XRF signal processor (e.g. possibly residing at a processing center) of the invention and adapted for operating the XRF signal processor to filter the spectrum of the XRF signal read by the handheld/portable XRF device and extract an XRF signature therefrom.

The technique of the invention facilitates use of handheld/portable XRF readers for reading XRF markings of objects in un-controlled environments (e.g. in-situ where the object to be examined is found/located). More specifically, certain embodiments of the present invention provide a novel solution, allowing to extract an accurate XRF signature (i.e. hereinafter also indicated as fingerprint) of the examined object, even from a relatively noisy signal of deteriorated SNR and/or SCR obtained from handheld/portable XRF readers which may be operated in un-controlled environments.

Thus, according to a broad aspect of the present invention there is provided a method for authenticating an object marked with XRF marking. The method includes: (i) filtering a wavelength spectral profile of a detected portion of an X-Ray signal arriving from an object in response to X-Ray or Gamma-Ray radiation applied to the object to suppress trend and periodic components from the wavelength spectral profile and thereby obtaining a filtered profile; and (ii) identifying one or more peaks in the filtered profiled satisfying a predetermined condition thereby enabling utilizing wavelengths of the one or more peaks to identify signatures of materials included in the object.

In some embodiments the method of the invention also includes irradiating the object with the X-Ray or Gamma-Ray radiation; detecting a portion of an X-Ray signal arriving from the object in response to the radiation applied to the object; and applying spectral processing to the detected X-Ray signal to obtain data indicative of wavelength spectral profile thereof within a certain X-Ray band.

According to some embodiments the filtering is carried out for wavelength spectral profiles that are associated with a plurality of portions of the X-Ray signal arriving from the object in a plurality of time frame portions of the X-Ray signal detected during a plurality of time frames. Then obtaining the filtered profile is achieved by computing an average of a plurality of filtered spectral profiles obtained by the filtering of the plurality of portions of the X-Ray signal that are obtained for the plurality of time frames.

According to some embodiments of the invention the wavelengths and possibly also the magnitudes of the one or more peaks are used to determine material data indicative of types and possibly also concentrations of materials included in the object. The material data is then utilized to authenticate the object.

According to some embodiments of the invention the filtering is performed by applying a time series analysis technique to the wavelength spectral profile of the detected signal portion to suppress said trend and periodic components from the wavelength spectral profile. The trend and periodic components, that are suppressed by the filtering, are associated with at least one of clutter and noise appearing in the detected portion of the X-Ray signal and sourced from one or more of the following: instrumental noise of the detection device, one or more foreign materials in the vicinity of the object, back-scattering noise, and interfering signals from neighboring peaks; said filtering thereby provides for improved Signal to Noise ratio (SNR).

In some embodiments the filtering includes providing a predetermined Auto-Regressive (AR) model for filtering spectra of XRF signals. For instance the predetermined Auto-Regressive (AR) model may be an Auto-Regressive-Integrated-Moving-Average (ARIMA) model. The Auto-Regressive and Moving-Average orders of the ARIMA model may be p=5 and q=12 respectively. Alternatively or additionally the Auto-Regressive weights of the ARIMA model may be determined based on an autocorrelation function of the wavelength spectral profile.

Also in some embodiments the filtering is performed by applying at least one of: Box-Jenkins processing and Seasonal-Decomposition processing to said portion of the detected X-Ray signal. For example the filtering may include seasonality filtration applied for suppressing the periodic component, and/or stationarity filtration applied for suppressing the trend component.

According to another broad aspect of the invention there is provided an X-Ray Fluorescence (XRF) device comprising a processor adapted for obtaining data indicative of a wavelength spectral profile of the X-Ray signal portion arriving from an object in response to irradiation of said object by X-Ray or Gamma-Ray radiation and detected by a radiation detector, and processing the wavelength spectral profile to identify signatures of materials included in the object. The processor includes a filtration module adapted for filtering said wavelength spectral profile to suppress trend components and periodic components from the wavelength spectral profile, wherein the trend components and periodic components are associated with at least one of noise and clutter in the X-Ray signal portion detected by said radiation detector. The processor thereby provides for obtaining a filtered profile with improved signal to noise and/or signal to clutter ratio from which spectral peaks associated with signatures of materials included in the object can be identified with improved accuracy and reliability.

Embodiments of the invention also provide methods for marking materials, preferably using a marker or markers which can be identified using X-ray fluorescence (XRF). The markers may be easily applied to materials, in a specific detectable quantity. Optionally, the marker comprises a composition comprising a marker compound comprising an atom that is detectable using XRF. The markers may be coded to provide a unique XRF signature ("fingerprint") which enables formation of a database which associates marked materials with appropriate manufacturers, batch numbers, manufacturing date, manufacturing site, serial numbers, customer data, port of origin, port of destination and other data relevant to the supply chain and/or the product. The marking may not be externally visible and may be detected using an XRF detector, preferably by a hand-held/portable XRF detector. The detector may be configured to communicate with a server in order to provide indication of authentication of the material.

Embodiments of the invention provide methods for marking waste materials, such as solid waste materials, or materials which potentially will require disposal. Marking waste materials may be performed using markers which can be identified using XRF. The markers may be easily applied to waste materials, before the material is disposed, by a relevant party, such as a municipality, and may stay adhered to or absorbed by the waste materials after the waste materials are dumped. The markers may be coded to provide a unique "fingerprint" which enables authorities to form a database that associates marked waste materials or potential waste materials, with entities (people or organizations) responsible for proper disposal of the waste.

Upon finding illegally disposed waste, an authority or an agent thereof may scan the waste for presence of a marker. Upon identification of a marker, the marker may be correlated to the identity of the entity responsible for proper disposal of the waste.

According to an embodiment of the invention, a method is provided for marking a solid waste material, comprising obtaining a material that can be identified using X-ray fluorescence, admixing the material with a liquid carrier to form a marking composition, and contacting the solid waste material with the marking composition.

Further embodiments of the invention provide methods for identifying an entity responsible for disposal of materials/objects such as solid waste. The method comprises: providing data indicative of unique XRF signatures of XRF markers used for marking materials/objects (e.g. solid material), which will potentially require disposal; providing association data that associates an entity responsible for disposal of the materials/objects/solid waste with the XRF signature of a marker or plurality of markers used for marking them (e.g. the association data may be stored in a database); receiving measurement data indicative of testing of a sample/portion of the solid waste material for presence of an XRF marker or a plurality of XRF markers; processing the measurement data to identify an XRF signature of the XRF marker or plurality of XRF markers, and using the association data (e.g. by querying the database at which it is stored) to identify the entity responsible for disposal of the solid waste material.

In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of, items it conjoins.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A to 1C illustrate schematically the technique for reading XRF markings according to certain embodiments of the present invention, wherein: FIG. 1A is a flow diagram of a method 100 for reading XRF markings, FIG. 1B shows schematic graphs illustrating components of an XRF signal being filtered according to the method 100 illustrated in FIG. 1A; FIG. 1C depicts graphs exemplifying an XRF signals A1 and A2 before and after it has being filtered by the method 100 respectively;

FIGS. 2A to 2C exemplify an XRF signal processing technique for filtering an XRF signal according to certain embodiments of the present invention, wherein: FIG. 2A shows a flow diagram of an XRF signal processing method 200 used in certain embodiments for filtering an XRF signal to extract therefrom an XRF signature with improved SNR and/or improved SCR; and FIGS. 2B and 2C are graphs exemplifying the operation of method 200 illustrated in FIG. 2A;

Dimensions of components and features shown in the figures are chosen for convenience and clarity of presentation and are not necessarily shown to scale.

DETAILED DESCRIPTION OF EMBODIMENTS

In the following detailed description, novel methods for marking and identifying objects/materials such as solid waste will be described in detail.

Figure 1A:
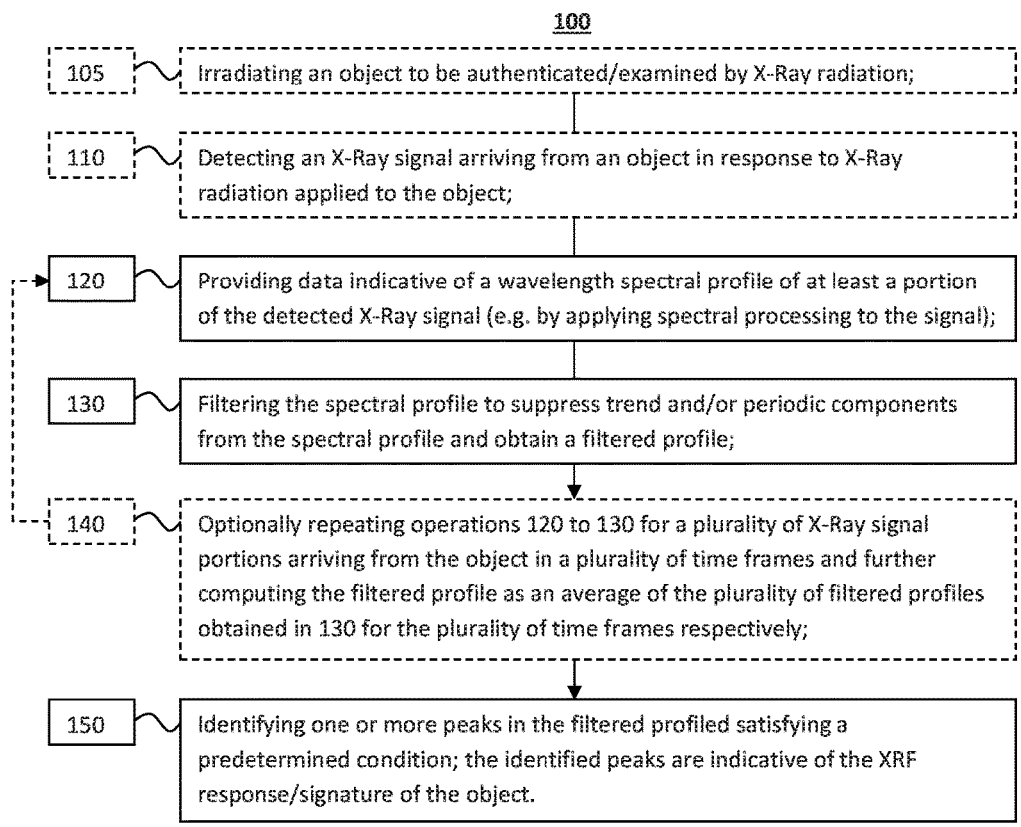

Reference is now made to FIG. 1A, which shows a flow-diagram depicting a method 100 for method 100 for reading XRF markings according to certain embodiments of the present invention. The method 100 provides a novel technique for reading XRF markings of an object under examination to allow identification and/or authentication and/or determination of certain properties associated with the object based on the XRF marking of the object. Method 100 allows extraction of an XRF signature of the object from a noisy XRF signal with improved SNR and improved SCR thereby facilitates in-situ examination of objects and/or material via mobile (portable/handheld) devices. Method 100 includes at least operations 120, 130 and 150 for filtering a wavelength spectral profile of an XRF signal, which is obtained/detected in response to X-Ray and/or Gamma-Ray radiation applied to the object, by utilizing statistical time series techniques to remove/suppress trend components and/or periodic components, and preferably both, from the wavelength spectral profile and identifying an XRF signature of the object from the filtered signal.

Optional operation 105 of method 100 includes irradiating an object to be examined by an X-Ray or Gamma-Ray radiation to excite XRF response from the object. It should be understood that various techniques may be used in operation 105 for irradiating the object with X-Ray/Gamma-Ray radiation, and may vary in different implementations of the method of the invention. A person versed in the art would readily appreciate types of radiation emitters, as well as the wavelength band and/or intensity of the radiation to be used usable given the requirements and conditions at which reading of XRF marking is required in the different implementations. For instance, the radiation emitter used should be operable for emitting X-Ray radiation with energy higher than the "energy" of the atoms/elements that form part of the XRF-marking and therefore need to be identified. Optionally, operation 105 includes application of precaution/safety measures before the irradiating the object to be examined by X-Ray or Gamma-Ray. For instance in some embodiments of the invention the XRF device includes a proximity/touch sensor which prevents activation of the radiation source/emitter unless a sample/part of the object to be examined is placed adjacent to the emitter (e.g. blocking the propagation path of the radiation).

Optional operation 110 of method 100 includes detecting and spectrally processing at least a portion of an XRF signal arriving from an object in response to X-Ray or Gamma-Ray radiation applied thereto. The XRF signal may be for example detected by detectors and/or spectrometers operable in a desired X-Ray band. The detected portion of the XRF signal is processed by utilizing suitable spectral processing techniques, such as a multichannel analyzer to determine the wavelength spectral profile thereof.

It should be noted that operations 105 and 110 are optional operations which are not necessarily carried out in all systems/devices implementing the method 100 of the invention. For example, some systems, implemented as central XRF signal processing systems, may be adapted for receiving data indicative of the spectral profile of the detected signal portion from an external XRF measurement unit/module implementing the operations of irradiating the examined object and/or detecting the XRF response. Also mobile XRF readers configured according to the present invention may be configured for detecting XRF signals arriving in response to X-/Gamma-ray radiation applied to the examined object by a separate radiation source module, and therefore such mobile XRF readers might not implement the operation 105 of irradiating the object.

To this end, in operation 120 data indicative of a wavelength spectral profile of at least a portion of the detected XRF signal, after it has been spectrally analyzed, is provided for processing according to the technique of the present invention to identify the XRF signature therein.

Operation 130 includes filtering the wavelength spectral profile to suppress trend and/or periodic components appearing therein and obtain a filtered profile. An advantage of the present invention relates to the novel filtering technique for filtering an XRF spectral profile which is described in the following in relation to this and the next operations of method 100, and also exemplified in details below with reference to FIGS. 2A to 2H. According to the invention significant parts of the noise and clutter in the detected XRF signal are distributed with identifiable characteristics within the wavelength spectral profile of the XRF signal. Particularly, significant portions of the noise and clutter appear in the form of trend and/or of periodic components within the wavelength spectral profile, which have characterizing features enabling to detect and suppress them from the wavelength spectral profile.

Figure 1B:
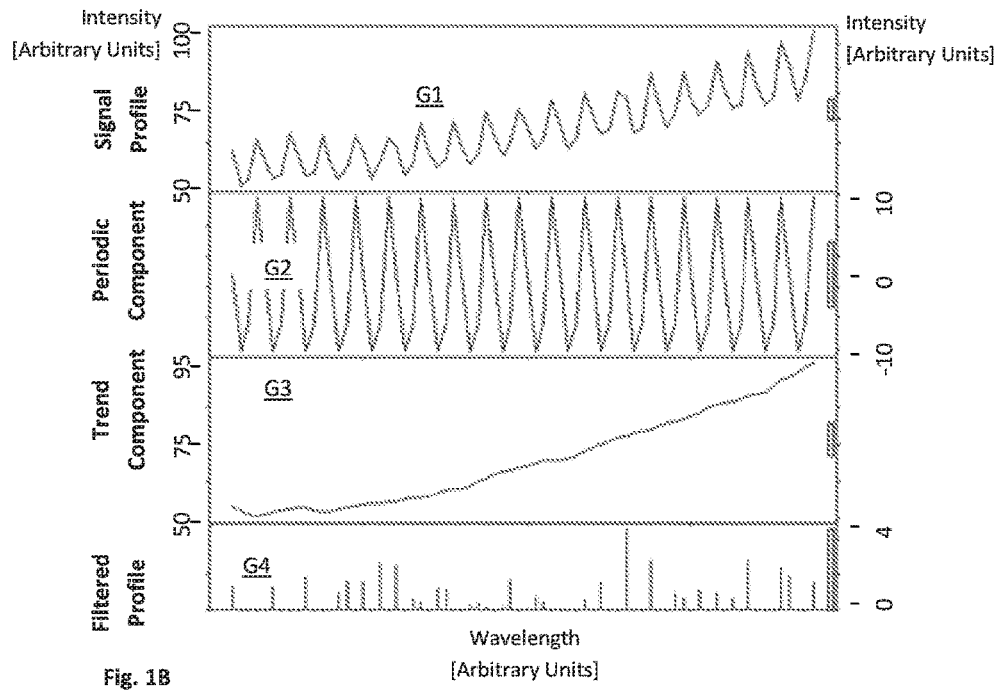

This is illustrated for example in FIG. 1B which shows schematic spectral graphs (intensity in arbitrary units as function of wavelengths) of different components of the wavelength spectral profile of the XRF signal, wherein:

G1—is a graph illustrating a section of a wavelength spectral profile of an XRF signal that is obtained from the detector. As shown here, the intensity of the XRF signal varies in scale between 50 and 100 in arbitrary units.

G2—is a graph illustrating a periodic component of the wavelength spectral profile, which has a certain periodicity. This periodic component may be associated for exampled with noise/clutter, such as electronic noise and/or back scattering. It is noted that the magnitude of the intensity of the periodic component that is illustrated in this graph varies between −10 and 10 in the same arbitrary units as in the above graph.

G3—is a graph illustrating a trend component of the wavelength spectral profile, which shows the tendency of the intensity of the XRF signal to rise/descend as a function of the wavelength. This trend component may be associated for example with noise/clutter. It is noted that the intensity of the trend component almost monotonically rises in this example from 50 to 95 in the same arbitrary units as in the above graphs.

G4—is a graph illustrating a filtered profile obtainable by applying operation 130 to suppress the periodic and trend components shown in G2 and G3 from the wavelength spectral profile of the XRF signal shown in G1. As shown here, subtracting/differentiating the trend components (G3) and the periodic components (G2) from the wavelength spectral profile (G1), provides a filtered spectral profile in which the spectral lines of the XRF signature appear more clearly and are not, or are less obscured by the trend and periodic components which are associated with noise. It should be noted that the intensity of the spectral lines of the XRF signature in the present example is a scale of between 0 to 4 (in the same arbitrary units used above) thus being in this example an order of magnitude lower from the trend component and also much lower from the periodic component.

In view of the above, it is clear that the XRF signature in the XRF signal of G1 is completely obscured by the periodic and trend components G3 and G2 (which are mostly with noise/clutter). Therefore, to be able to read the XRF signature from such an XRF signal without suppressing these components requires using higher intensity X-Ray/Gamma-Ray emitters, more accurate and less noisy detectors, and/or conducting the measurement in less noisy conditions providing reduced clutter. The technique of the present invention provides for solving these problems by removing the trend and periodic components from the XRF signal. Even more specifically, as described in more detail below, the present invention also provides a novel technique identifying and filtering these noise components for removing the periodic and/or the trend components by utilizing statistical techniques which are borrowed from field of time-series statistical analyses and which are conventionally used to time sequences. For instance, in certain embodiments of the present invention, in operation 130 predetermined models such as auto-regressive models and/or moving average models (e.g. ARIMA) are provided and used to identify/filter the periodic and/or trend components of the wavelength spectral profile of the XRF signal.

Figure 1C:
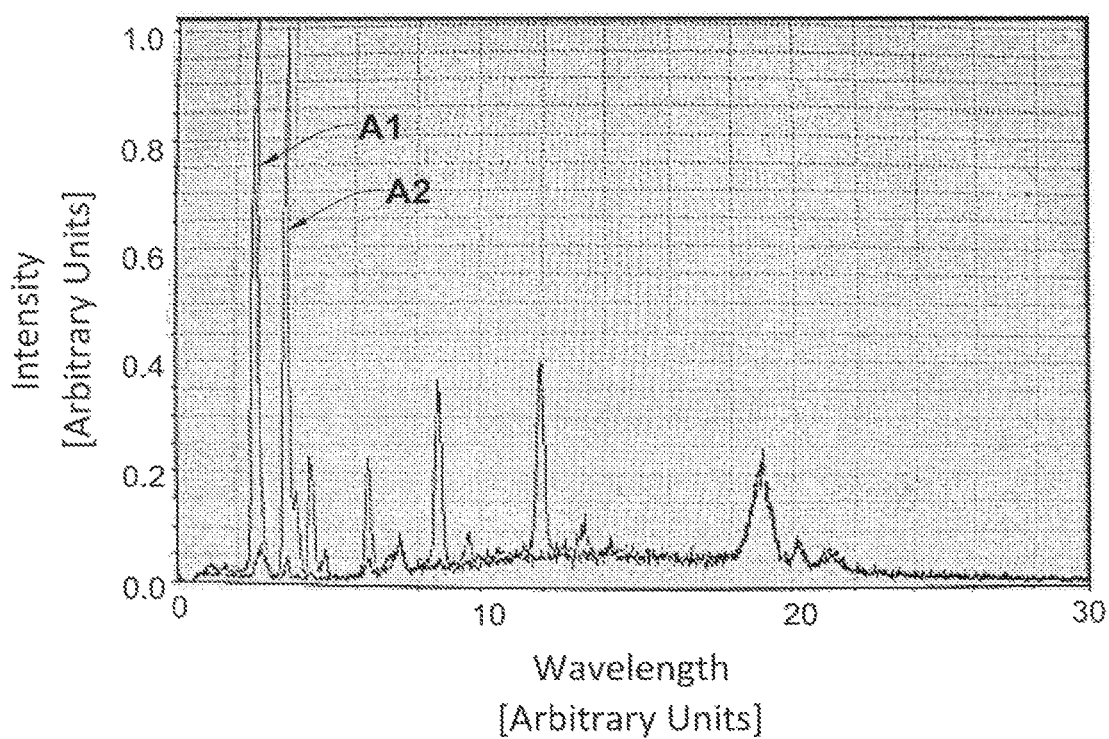

As indicated above, ARIMA models (generally referred to as an ARIMA (p,d,q) where parameters p, d, and q are non-negative integers that refer to the order of the autoregressive, integrated, and moving average parts of the model respectively) are conventionally used in statistical processing of time series to better understand the data, or to predict future points in the time series. Here the ARIMA model is used to process the wavelength spectrum of the XRF signal, and the parameters of the model, p, d and q, are selected to filter out trend and/or periodic components from the XRF signal. In some embodiments of the invention the parameters of the model, p, d and q, are specifically selected/determined for filtration of the wavelength spectral profile of the XRF signal. The parameters may be determined (e.g. predetermined in advance for example by trial and error and/or by computer simulations), so that they fit extraction/filtration of periodic and/or trend (noise/clutter) spectral components of the XRF signal. Also, in certain embodiments of the present invention, in operation 130 time series methods, such as Box-Jenkins and/or Seasonal Decomposition methods and/or variants of such methods, are used for filtering the XRF signal to suppress the periodic and/or trend spectral components from the signal. For example, the Box-Jenkins and/or Seasonal Decomposition methods may be applied for processing the wavelength spectrum of the XRF signal based on a selected ARIMA model to thereby obtain a filtered spectral profile of the XRF signal from which the XRF signature can be extracted. FIG. 1C depicts graphs A1 and A2 of an actual XRF signal respectively before and after it was filtered by method 100. An example of an implementation of method 100 is described in detail with references to the flow diagram of FIG. 2A.

In this regard it should be noted that the fact that noise and clutter in the XRF signal are expressed in the form of periodic and/or trend components in the wavelength spectra of XRF signal, is surprising and would not be obvious to a person of ordinary skill in the art. Accordingly, also the use of time series techniques to identify and/or filter the trend component (also referred to herein as non-stationary) and/or the periodic component components (also referred to herein as seasonality component) from the spectra would not be obvious to a person of ordinary skill in the art.

It is noted that, in the time-series statistical analysis field, the trend and periodic components of the time series are often referred to as non-stationary and seasonal components respectively; accordingly, these terms are also used interchangeably herein to respectively indicate the trend and periodic components of the spectrum, even though these trend and periodic components of the spectra present trend and/or periodicity with respect to the wavelength scale and not the time scale.

Optionally, in some embodiments operation 140 is carried out in order to further improve accuracy and reliability of the XRF signature which is subsequently obtained in operation 150 described in the following. The optional operation 140 includes repetitions of the above described operations 120 to 130 for filtering the wavelength spectral profiles of a plurality of X-Ray signal portions, which arrive from the object in a plurality of time frames. The final filtered profile of the XRF signal is then computed by integrating (e.g. summing/averaging) the filtered profiles obtained in operations 130 by filtering the wavelength spectra of the respective plurality of time frames. In this way the SCR/SNR in the final filtered profile is further improved as compared to a filtered profile of a single time frame, thereby enabling to obtain the XRF signature with improved reliability and accuracy.

In operation 150, data indicative of the XRF-signature of the object is obtained from the filtered profile obtained in operation 130 or in optional operation 140 (e.g. the final filtered profile). Operation 150 includes identifying peaks in the filtered profile which satisfy a predetermined condition(s) and utilizing those peaks to determine the XRF signature of the examined object.

For instance, in some embodiments of the present invention the predetermined conditions include identifying peaks, whose max intensity and/or slop exceeds certain predetermined threshold(s). In this case, in 150, peaks whose intensity/slop is below the threshold(s) are ignored and the remaining wavelengths, and possibly also the intensities of the remaining peaks, whose height/slop is above the threshold(s) are used to provide data indicative of the XRF signature.

Alternatively or additionally, in certain embodiments the predetermined conditions are based on the XRF spectral response of predetermined set of reference materials which are considered as part of the XRF-marking of the object. Reference data, such as a lookup table (LUT), indicative of the reference spectral responses of one or more different reference materials, may be stored in a memory. For example for each reference material the reference data may include wavelengths of one or more spectral peaks that are generally included in the spectral XRF response of the material, and possibly also the relative height of those peaks (the heights in the reference data may be normalized to a certain scale (e.g. to a certain concentration of the reference materials). In such embodiments operation 150 includes processing the filtered profile based on the reference data to determine correlation values indicative of the degrees of correlation between the reference spectral responses of the reference materials, with the filtered profile. The correlation values may serve, and/or may be used to determine the data indicative of, the XRF signature of the examined object and may actually be indicative of the concentrations of the reference materials in the examined object.

The wavelengths and magnitudes of the one or more peaks are used in 150 to determine XRF signature data indicative of types and/or concentrations of XRF marking materials included the object. The types and/or concentrations of the XRF marking materials (namely the XRF signature data) can further be used to identify and/or authenticate the object.

To this end, the object may be marked by an XRF-marking compound (hereinafter referred to also as XRF-marker and/or marker compound and/or marker) detectable using X-ray fluorescence. Optionally, the marker compound may be a substituted alkane, in which at least one hydrogen atom is substituted by an element which can be detected by an X-ray fluorescence analyzer (XRF). The resultant compound may have a general formula $CnH2n+2-mXm$ wherein $n=1, 2, 3 \ldots$, and $m=1, 2, 3 \ldots$ "X" is any element which can be detected by an X-ray fluorescence analyzer (XRF). For example, X may be lithium (Li), an alkali metal, which forms one covalent bond with a carbon atom.

According to another example the marker can be a halogenic compound, such as an alkyl halide having the general formula $CnH2n+2-mXm$, where $n=1, 2, 3 \ldots, m=1, 2, 3 \ldots$ "X" is a halogen such as fluorine (F), chlorine (Cl), bromine (Br), and iodine (I). An example of such an alkyl halide is tetrabromoethane having the molecular formula $C2H2Br4$. The marker may also be an aryl halide having the general formula $C6H6-mXm$ wherein $m=1, 2, 3, 4, 5$ or $6$, and "X" is a halogen such as fluorine (F), chlorine (Cl), bromine (Br), and iodine (I).

Optionally, the marker compound may be an alkyl or aryl halide selected from the group consisting of: 1,1,2,2 tetrachloroethane (i.e., $C2H2Cl4$), 1,1,2 trichloroethane (i.e., $C2H3Cl3$), pentachloroethane (i.e., $C2HCl5$), hexachloroethane (i.e., $C2Cl6$), 1,2,4 trichlorobenzene (i.e., $C6H3Cl3$), 1,2,4,5 tetrachlorobenzene (i.e., $C6H2Cl4$), ethyliodide (i.e., $C2H5I$), ethylbromide (i.e., $C2H5Br$), dichloro 1,2 dibromoethane (i.e., $C2H2Cl2Br2$), dichlorotribromoethane (i.e., $C2HCl2Br3$), difluoro-1-chloroethane (i.e., $C2H3F2Cl$), difluoro 1,2 dibromoethane (i.e., $C2H2F2Br2$), trifluoro 1,2,2 dibromoethane (i.e., $C2HF3Br2$), tribromopropane (i.e., $C3H5Br3$), dibromobenzene (i.e., $C6H4Br2$), dibromoethane (i.e., $C2H4Br4$), n-propylbromide (i.e., $C3H7Br$), parabromofluorobenzene (i.e., $C6H4FBr$) butylbromide (i.e., $C4H9Br$) and octylbromide (i.e., $C8H17Br$).

According to another example, the marker can be an organometallic or a halogenic compound in which at least one metallic element or at least one halogen, bonds with at least one carbon atom of an alkene (olefine), having the general formula $CnH2n-mXm$, where $n=1, 2, 3 \ldots, m=1, 2, 3 \ldots$ "X" is either an alkali metal or a halogen. An example of such a compound is bromoethylene having the molecular formula $C2H3Br$.

According to a further example, the marker can be any of the above mentioned compounds wherein silicon (Si), germanium (Ge), and the like, substitute an atom of carbon. For example, diethyl silane (i.e., $C4H12Si$) is such a compound. It will be noted that silicon is detectable by the X-ray fluorescence analyzer and no substitutions for hydrogen atoms are necessary. Accordingly, "X" elements do not need to appear in the compound, if the silicon, germanium or other element serve as the marking element detectable by the X-ray fluorescence analyzer. For alkanes, the general formula of the compound is $Cn-mH2n+2Ym$, where $n=1, 2, 3 \ldots, m=1, 2, 3 \ldots, m<n$ and where "Y" designates the silicon, germanium or other element. For alkenes (olefines), the general formula of the compound is $Cn-mH2nYm$, where $n=1, 2, 3 \ldots, m=1, 2, 3 \ldots$ and where "Y" designates the silicon, germanium or other element.

According to an embodiment of the invention, the marker comprises a salt comprising an atom having an atomic number comparable to lithium, or higher. According to an embodiment of the invention, the marker comprises a salt comprising an atom having an atomic number comparable to magnesium, or higher In some embodiments detectable compositions usable for marking the object by XRF-markers are formed by admixing an XRF-marker compound with a carrier. The detectable composition may be in liquid form. Preferably, the composition comprises an agent that assists in the adhering of the composition to the material to be marked, or an agent which assists in the absorption of the composition in the material to be marked. The agent, according to an embodiment of invention, may be a binder. The binder may comprise one or a combination of: alkyds, acrylics, vinyl-acrylics, vinyl acetate/ethylene (VAE), polyurethanes, polyesters, melamine resins, epoxy, or oils. Detectable compositions may further comprise a pigment and/or a solvent. For example detectable compositions may be in the form of a paint, glue or epoxy.

To this end, the reference data used in 150 may include data indicative of various detectable compositions and/or markers which are used by the technique of the present invention to mark and identify objects. In some embodiments, the technique of the invention enables detection of XRF-markers, which present in the object in concentrations in the range of between about 100 parts per billion (ppb) to 100 parts per million (ppm).

Figure 2A:
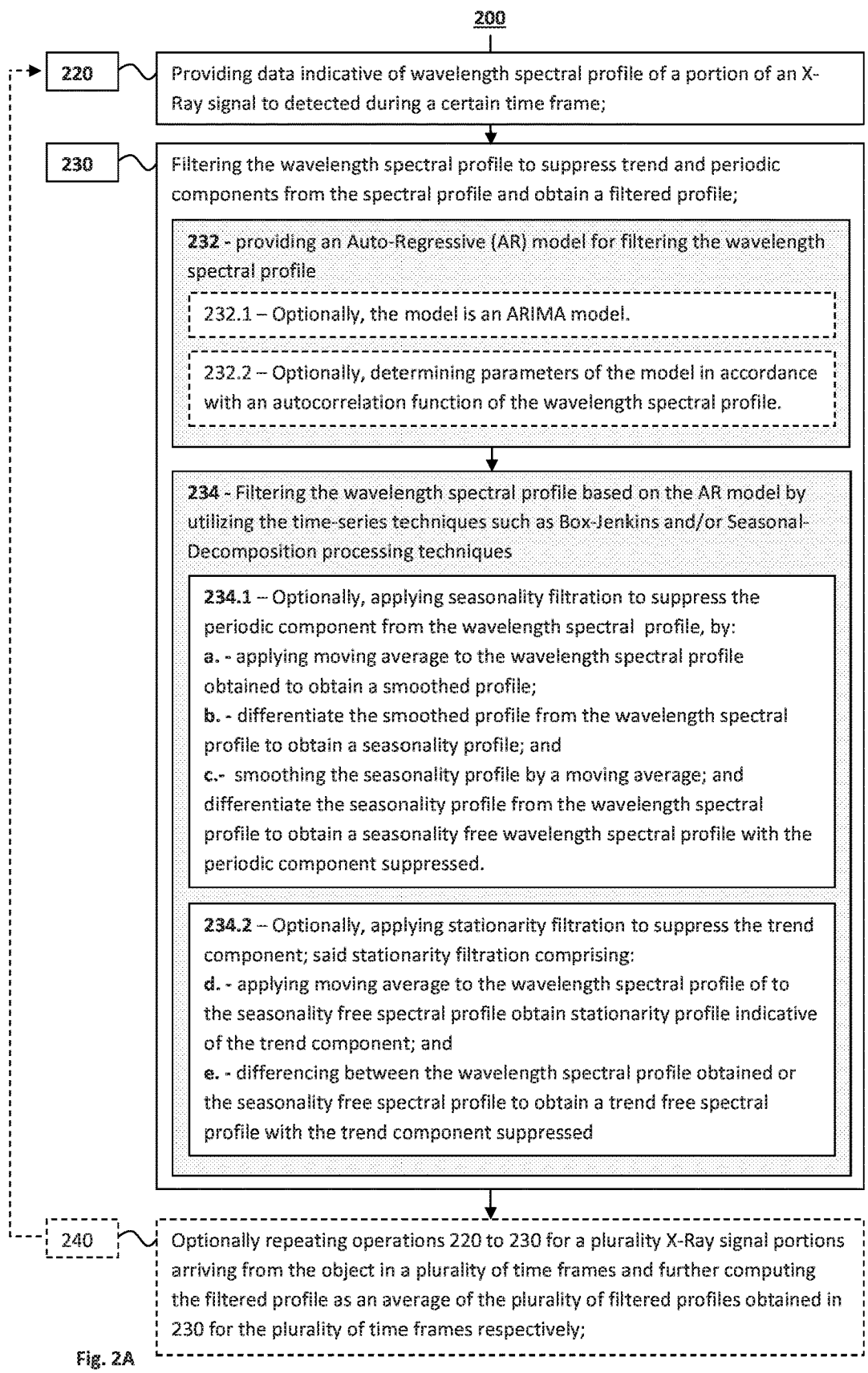

FIG. 2A is a flow chart illustrating in more detail a method 200 for processing XRF signals according to certain embodiments of the present invention. The method includes operations 220, 230 and optional operation 240, in which: in operation 220, data/signals indicative of a wavelength spectral profile of at least a portion of a detected XRF signal is provided, in 230 the wavelength spectral profile the portion of the detected XRF signal is filtered to suppress trend and periodic components, and optional operation 240 includes repetitions of operations 220 and 230 for filtering the wavelengths spectral profiles of a plurality X-Ray signal portions, which arrive from the object in a plurality of time frames, and integration (e.g. averaging of the plurality of filtered spectral profiles obtained in this way to obtain a final filtered profile with improved SNR and/or improved SCR). Operations 220 and 240 are generally similar to operations 120 and 140 described above and therefore need not be described in the following in more detail. Operation 230 of method 200 is a particular example of an implementation of operation 130 of method 100 described above.

Operation 230 includes sub operation 232 for providing an Auto-Regressive (AR) model for filtering the wavelength spectral profile provided in 220. As indicated in 232.1, optionally the model used is an ARIMA model. The parameters of the model are obtained for filtering the XRF signal. The parameters may be predetermined parameters previously determined to fit filtration of an XRF signal (e.g. stored in memory) and/or, optionally, in 232.2 certain of the parameters may be determined based on the wavelength spectral profile which is to be filtered. For example the autoregressive parameter p, may be determined (e.g. dynamically determined in real time) by calculating the autocorrelation function of the wavelength spectral profile and identifying the location(s) of extremums (e.g. maxima) in the autocorrelation function.

For instance in some embodiments the Auto Regressive P, Integration d, and Moving Average q parameter/orders of the ARIMA model are set as follow: $p=5$ and $q=12$. In certain embodiments q consecutive Moving Average (MA) weights selected from the repeated series of weights are used for the MA part of the ARIMA model. The inventors of the present invention have realized that in some cases using this set of MA weights provides good results when filtering XRF wavelength spectra.

Operation 230 includes sub operation 234 in which the wavelength spectral profile is filtered the based on the AR (e.g. ARIMA) model by utilizing time-series processing techniques, being an adaptation of the Box-Jenkins and Seasonal-Decomposition processing techniques to filtration of the XRF-signal.

Figure 2B:
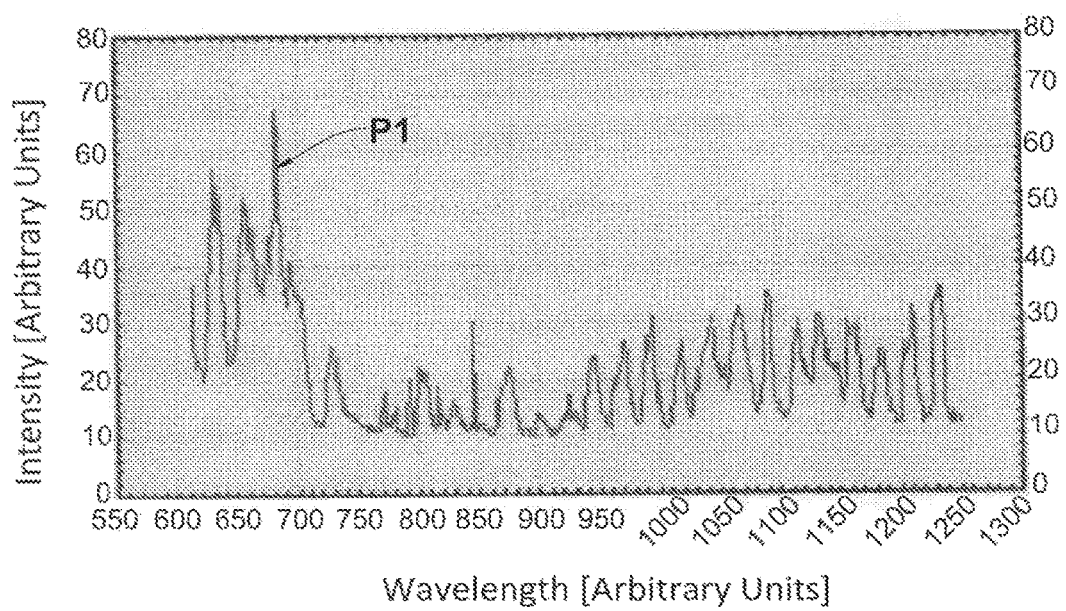
Figure 2C:
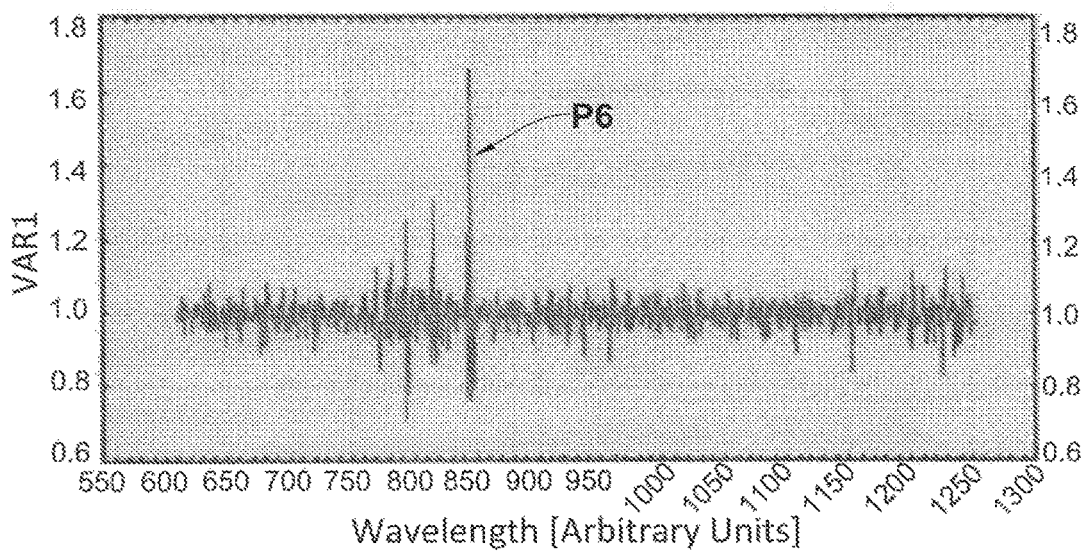

For instance, in optional sub operation 234.1 seasonality filtration is applied to suppress the periodic component from the wavelength spectral profile. In this example, seasonality filtration may include:

a.—applying moving average to the wavelength spectral profile to obtain a smoothed profile of the wavelength spectral profile. An example of a wavelength spectral profile of an XRF signal that is provided in 220 is illustrated in FIG. 2B. In this example, the moving average is applied by averaging $q=12$ consecutive samples of the XRF signal with $q=12$ weights that are given in the ARIMA model provided in sub operation 232.

b.—then, the smoothed profile is differentiated, in this case by subtraction of the smoothed profile from the wavelength spectral profile P1 to obtain a seasonality profile indicative of the periodic peaks which are associated with noise and/or clutter and which exist in the wavelength spectral profile P1. It should be noted that although the inventors have found that in some implementations it is preferable to perform the differentiation by subtraction of the smoothed profile from the wavelength spectral profile P1, yet in some embodiments the differentiation may be performed in another way to obtain the seasonality profile, for instance by division of the wavelength spectral profile P1 by the smoothed profile (e.g. or vice versa).

c.—finally, in order to suppress the periodic components from the wavelength spectral profile P1 and obtain a "seasonality free" wavelength spectral profile the seasonality profile obtained in (b.) is smoothed by applying a moving average to obtain a smoothed seasonality profile and then differentiating the smoothed seasonality profile from the wavelength spectral profile P1 thereby obtaining the "seasonality free" wavelength spectral profile from which at least some periodic components are suppressed.

In optional sub operation 234.2, stationarity filtration is applied to suppress the trend component from the "seasonality free" wavelength spectral profile (or from the wavelength spectral profile P1, e.g. in case steps a. to c. above were not performed). In this example the stationarity filtration includes:

d.—applying moving average to the "seasonality free" wavelength spectral profile (e.g. this may also be applied to the wavelength spectral profile P1) to obtain stationarity profile indicative of at least a part of the trend component existing in the wavelength spectral profile P1.

e.—Then, differencing between seasonality free spectral profile (e.g. or the wavelength spectral profile P1) and the stationarity profile, in order to suppress the trend component from the "seasonality free" wavelength spectral profile (e.g. or from the wavelength spectral profile P1) and obtain a trend free spectral profile P6 in which the trend component is suppressed. The "trend free" spectral profile P6 obtained at this stage is illustrated for example in FIG. 2C. It should be noted that here the differentiation is performed by subtracting the stationarity profile from the "seasonality free" wavelength spectral profile, and that to this end the profile P6 is actually a filtered wavelength spectral profile of the XRF-signal from which both seasonality (periodic) components and stationarity (trend) components are suppressed. It should also be understood that although the differentiation of this step is performed in this example by subtraction, in some embodiments the differentiation to remove the trend component may be performed by other techniques, for example by division of the "seasonality free" wavelength spectral profile (e.g. or from the wavelength spectral profile P1) by the stationarity profile.

Thus, at the end of operation 234 exemplified above a filtered wavelength spectral profile P6 is obtained from which significant parts of both the trend and the periodic components, which are associated with noise/clutter, are removed. Remaining prominent peaks are mainly indicative of the actual XRF signature of the examined object. In the following operation similarly 150 described above may be performed to extract data indicative of the XRF signature from the filtered profile P6 with improved accuracy and reliability.

Comparing the spectral profiles P1 and P6, before and after filtration by the technique of the present invention, it is noted that much of the noise and clutter is suppressed in profile P6. In the profile P6 after filtration, peaks in the area of 850 along the y-axis are visible. The sensitivity is improved as can be seen by comparing the scale of the Y-axis of FIG. 2B, which is in the range of about 0-80, and the scale of the Y-axis of FIG. 2C, which is around the range of 0-2. This increased sensitivity allows for user of smaller amounts of marking substances, as peak resolution is increased.

Figure 3:
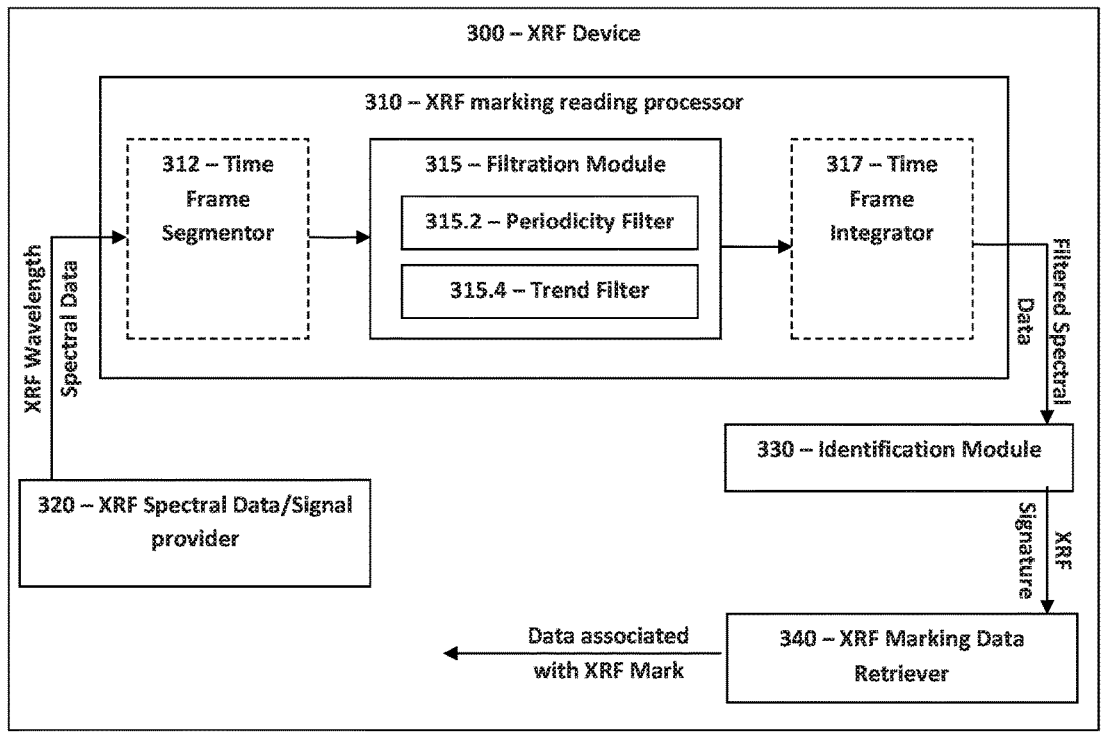
FIG. 3 is a block diagram of an XRF device comprising an XRF signal processor configured according to an embodiment of the present invention.

Turning now to FIG. 3, a block diagram exemplifying an X-Ray Fluorescence (XRF) device 300 configured according to some embodiments of the present invention is exemplified. The XRF device 300 includes an XRF Spectral Data/Signal provider 320 that is adapted to provide data indicative of a wavelength spectral profile of an XRF signal portion that arrived from an object in response to irradiation of the object by X-Ray or Gamma-Ray radiation and detection of the response XRF signal by a radiation detector. The XRF device 300 also includes an XRF-marking reading processor 310 (hereinafter 'processor') that is adapted process the wavelength spectral profile in accordance with the technique of the present invention (e.g. implementing method 100 and/or method 200 described above) to a filtered profile indicative of the XRF signatures of materials (e.g. XRF markers) included in the object. The XRF device 300 also includes an identification module 330 adapted to process the filtered profile to identify the XRF signature therein and provide data indicative thereof. The identification module 330 may be adapted, for example, to carry out the operation 150 of method 100 described above to identify, in the filtered profile, peaks satisfying a predetermined criteria, and utilizing the wavelengths, and possibly also the magnitudes of those peaks, to identify the XRF signature of the object. Also the device 300 may also include an XRF Marking Data Retriever 340 associated with a memory storing reference data indicative of various detectable compositions and/or markers which are used to mark objects, and which may be adapted to process the data indicative of the XRF signature obtained by identification module 330 based on the reference data, and determining the XRF-marker used to mark the object and providing and/or storing data indicative thereof.

According to some embodiments of the present invention the processor 310 includes a filtration module 315 including at least one of a periodicity filter 315.2 and a trend filter 315.4 that are respectively adapted for filtering the wavelength spectral profile to suppress periodic components and trend components therefrom. For example in some embodiments the filtration module 315 includes a periodicity filter 315.2 and a trend filter 315.4 that are respectively configured and operable for implementing operations 234.1 and 234.2 described above in order to suppress the periodic and trend components from the wavelength spectral profile of the XRF signal portion.

According to some embodiments of the present invention the processor 310 also includes a time frame segmentor 312 and a time frame integrator 317 which are configured and operable for implementing method operations 140 and/or 240 in order to further reduce the noise and/or clutter from the final filtered signal. To this end, the time frame segmentor 312 is configured and operable to segment the XRF signal provided by the XRF Spectral Data/Signal provider 320 into a plurality of (i.e. two or more) wavelength spectral profiles. The filtration module 315 then filters each of the wavelength spectral profiles independently to remove/suppress the trend and/or periodic components therefrom. Then the time frame integrator 317 integrates (e.g. averages) the filtered profiles obtained by the filtration module for each of the signal portions of the different time frames to obtain a final filtered profile with improved SNR and/or SCR.

It should be noted that generally the XRF device of the present invention may be implemented by analogue and/or digital means. In some cases the XRF device includes a computerized system including a computer processor (CPU) and a memory. The modules of the device may thus be implemented by suitable circuitry and/or by software and/or hardware components including computer readable code configured for implementing the operations of methods 100 and/or 200 described above.

The XRF device of the present invention may be implemented as part of an XRF signal processing center, and/or as a portable (e.g. handheld) XRF reading device.

Figure 4A:
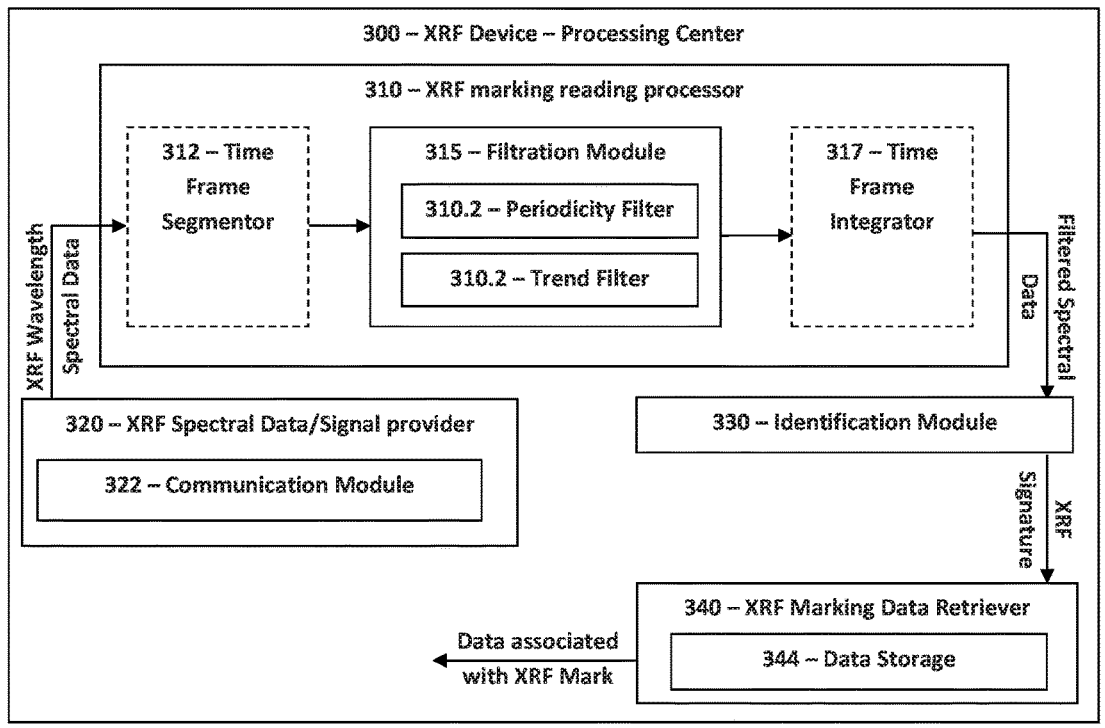
FIGS. 4A and 4B are block diagrams respectively exemplifying the configurations of a processing center XRF device and a mobile (e.g. handheld) XRF device according to embodiments of the present invention.

An XRF device 300 of the invention implemented in an XRF signal processing center is illustrated in a block diagram in FIG. 4A. Description of the configuration and operation of common elements/modules of the device 300 which are similar to those of the device shown in FIG. 3 will be repeated here. In the implementation of the XRF device of in an XRF signal processing center, the XRF Spectral Data/Signal provider 320 includes and/or is associated with a communication module 322, and is operable receiving data indicative of the XRF signal via communication with a remote XRF reading device which is used to detect the XRF signal response from the object. Also in this implementation the XRF Marking Data Retriever 340 includes and/or is associated with data storage (memory) 344 storing the reference data marking data indicative of a plurality of XRF markers to be identified by the XRF device 300. Possibly the data storage (memory) 344 also stores association data associating information indicative of a plurality of objects with XRF markers. Data retriever 340 browses/queries the data storage 344 to determine the XRF marker that best fits the XRF signature obtained by the identification module 330. Optionally the data retriever 340 also browses/queries the data storage 344 to determine properties of the object based on the identified XRF marker and the association data stored in the data storage. Then data indicative of the identified XRF marker and/or of the properties of the identified object may be communicated (e.g. via the communication module 322 and/or via a different module) to the XRF reader providing the XRF signal.

Figure 4B:
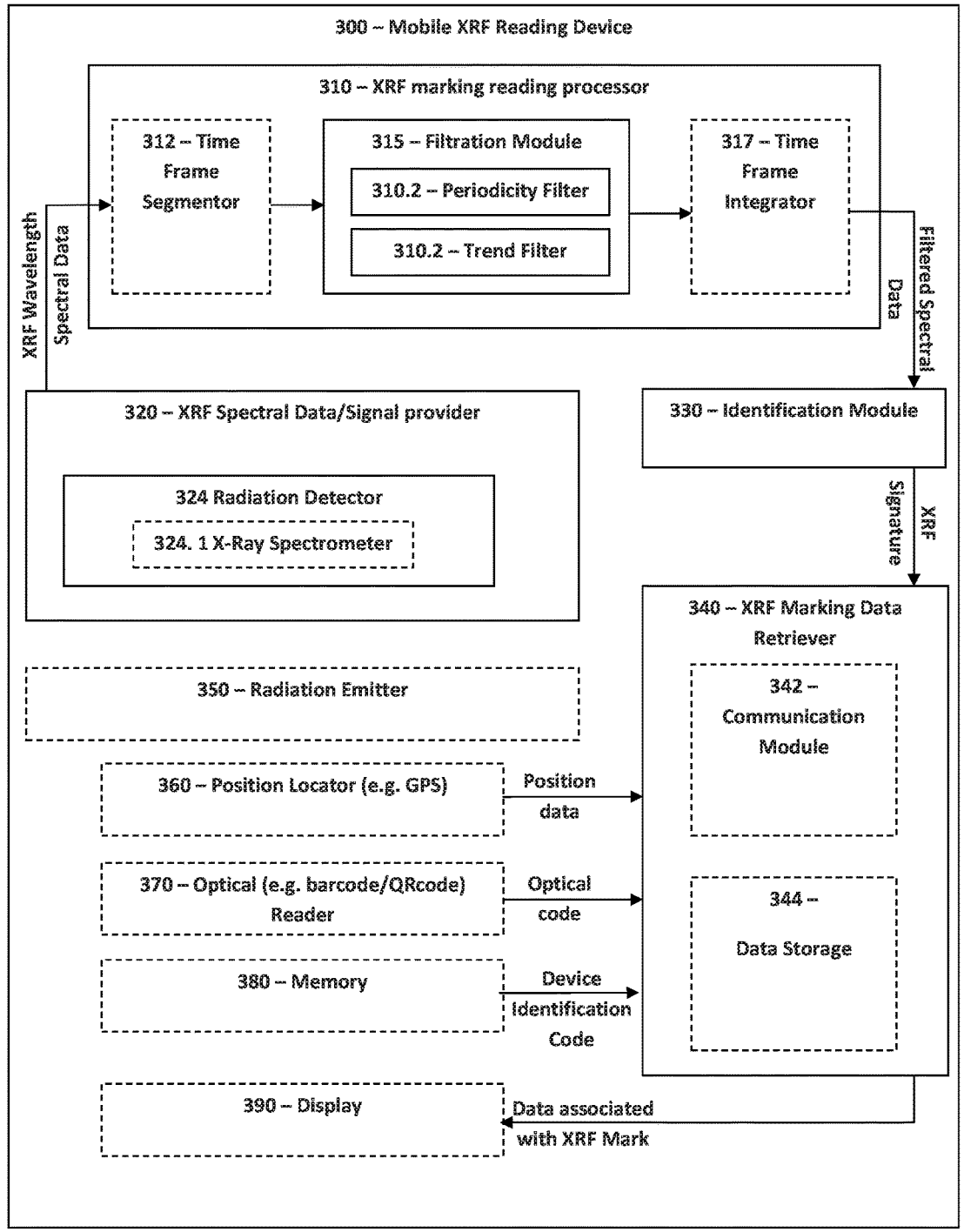

An XRF device 300 of the invention implemented as a handheld/portable XRF reader is illustrated in a block diagram in FIG. 4B. Description of the configuration and operation of common elements/modules of the device 300 which are similar to those of the device described above with reference to FIG. 3 will not be repeated here. In the implementation of the XRF device 300 as a handheld/portable device, the XRF Spectral Data/Signal provider 320 may include a radiation detector 324, such as an X-Ray spectrometer adapted to detect and spectrally analyze an XRF signal arriving from an object in response to irradiation of the object by X-Rays or Gamma-Rays, and provide data signals indicative of the wavelengths spectral profile of the detected signal. In some embodiments the radiation detector 324 enables detection an XRF marker material marking said object and having concentration in the order of about 1 ppm or even below, in the order of about 100s of ppb.

In some embodiments the XRF device 300 may optionally also include a radiation emitter 350 configured and operable for emitting said X-Ray or Gamma-Ray radiation for irradiating an object to be examined by the portable XRF device 300. In this implementation the XRF marking data retriever 340 may include a communication module 342 and/or a data storage 344 which are utilized to obtain, based on the identified XRF signature, the XRF marking data associated with the XRF marker marking the object and/or object data indicative of the properties of the object. For this purpose the data storage 344 may store reference data and/or association data associating various XRF signatures with specific XRF markers and/or associating the XRF-signatures and/or various markers with properties of the objects marked thereby. Alternatively or additionally, the handheld device 300 may use the communication module 342 (e.g. wireless communication module) to communicate data indicative of the XRF-signature and/or the filtered profile to a processing center and receive therefrom data indicative of the object and/or marker data indicative of the XRF marker used for marking the object.

In some cases, the marker data obtained by the XRF marking data retriever 340 is indicative of one or more of the following: the XRF signature of object in its raw form; one or more additive XRF marking materials added to the object to mark it; and/or a carrier material used for adhering XRF marking materials to the object. In some cases the object data obtained by the XRF marking data retriever 340 includes data indicative of one or more of the following: identity of the object; identity of a product said associated with object, identity of manufacturer of said object; batch number of the object, manufacturing date of the object, manufacturing site of the object and/or serial number of the object; and identifier of an owner of said object. In some embodiments the XRF device 300 includes a display module 390 (e.g. including a display screen and a display controller (not shown)) which are configured and operable to obtain the marker data and/or the object data from the XRF marking data retriever 340 and present on the display screen indicia indicative of the object.

In some embodiments the XRF device 300 includes a position locator 360 (e.g. GPS) configured to determine/estimate the position of the XRF device 300 and utilize the communication module (e.g. 342) to communicate data indicative of the position to the processing center together with the data of the filtered profile/XRF signature. In some embodiments the XRF device 300 includes an optical reader 370 (e.g. barcode/QRcode reader) configured to read an optical code, such as barcode/QRcode) of the object and communicate the data indicative of the optical code to the processing center together with the data of the filtered profile.

In some embodiments the XRF device 300 also includes a memory storing a unique identification code of the XRF device 300. The XRF device 300 may be configured to communicate the unique identification code to the central computer via the communication module together with the data of the filtered profile.

Figure 5:
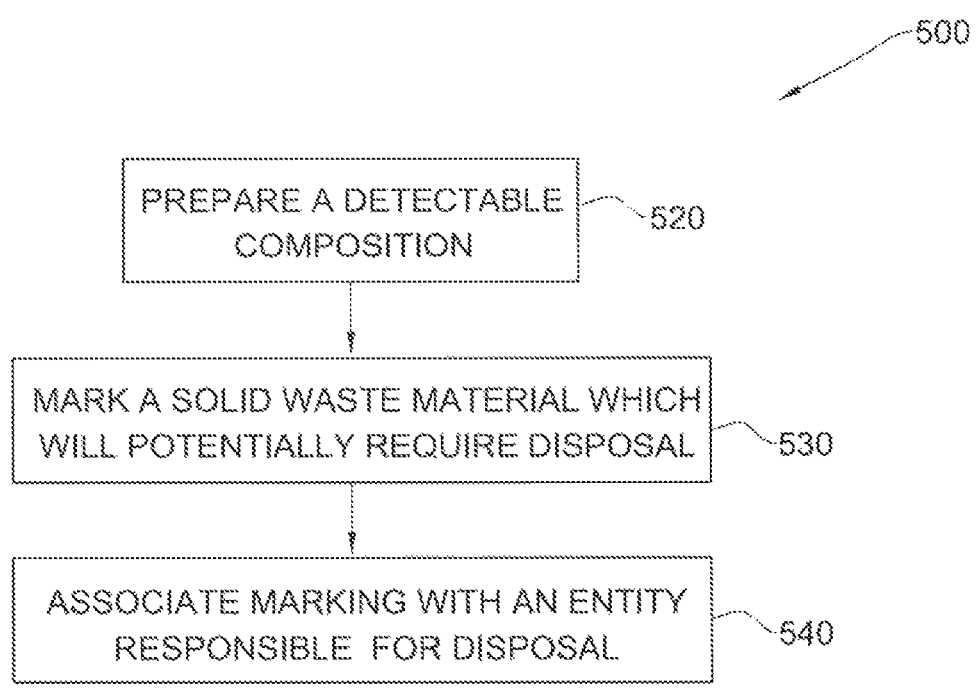
FIG. 5 shows a flow diagram depicting a process according to embodiments of the invention.

Reference is now made to FIG. 5 which shows a flow-diagram depicting a method 500 for the marking of waste materials/objects.

Method 500 includes 520 providing/preparing a detectable composition for marking the waste materials. Optionally, the detectable composition comprises an XRF marker compound that comprises an atom that is detectable using X-ray fluorescence. According to an embodiment of the invention, the XRF marker compound is present in the detectable composition in an amount enabling detection by an XRF device such as device 300 described above. According to an embodiment of the invention, the XRF marker compound is present in the composition in an amount such that the concentration of the element which can be detected by an XRF device is present between the range of about 100 parts per billion (ppb) and 100 parts per million (ppm).

According to an embodiment of the invention, method 500 further includes 530 marking waste and/or, object(s)/or solid materials which will potentially require disposal, by the detectable composition (e.g. XRF marker compound) provided/prepared in 520. According to an embodiment of the invention, marked object/materials may comprise construction materials which may be or become construction waste as a result of destruction or renovation of roads, buildings and other man-made structures. Such construction materials may comprise concrete, asphalt, metal, wood, insulation materials, drywall, glass, plastic and other associated debris. Additional embodiments of the invention also relate to liquid materials/waste. In some embodiments of the invention, the marked object/materials are not yet in waste form at the time of marking. For example, if a building is scheduled to be demolished, the building materials that form the building may be considered solid waste material and may be marked with the detectable composition, before demolition of the building.

According to an embodiment of the invention, the detectable (e.g. by XRF marker) composition is in the form of paint. In such embodiments in 530 the objects/materials/solid waste is marked by applying/painting the object with a detectable XRF marking composition in the form of paint (for example by spraying). Applying a detectable/XRF-marking composition to the solid waste material in the form of paint requires immense effort to remove the detectable composition from the solid waste material, thereby discouraging removal of the composition and subsequent illegal disposal. In some embodiments of the invention, the detectable/XRF-marking composition is in the form of a colored paint. The colored paint may be colored a different color than the object/material to which it is applied, thereby enabling easy identification of marked objects/materials disposed as waste. Alternatively, in some embodiments, the colored paint may be colored with a color similar to the surface of the object to which it is applied. For example, if the object is a road having white or yellow striping, the detectable composition may be applied in a paint having the same color as the striping, thereby "masking" the marking and making the marking difficult to find and/or remove.

According to an embodiment of the invention, the detectable composition is a stable composition which maintains its stability and its ability to be detected through X-ray fluorescence after being applied to the waste material for a period of at least a year. According to an embodiment of the invention, the detectable composition maintains its ability to be detected through X-ray fluorescence after being applied to the waste material for a period of at least 3 years.

According to an embodiment of the invention, an appropriate detectable composition is matched to a specific type of construction waste being marked. For example, if the construction waste is concrete, a sample of non-marked concrete is analyzed by X-ray fluorescence for detectable presence of atoms. A result is obtained that the concrete does not contain detectable levels of two elements, Li and Br. As a result of the analysis, a detectable composition comprising a known amount of Li and Br is formed and is applied to the concrete construction waste.

According to an embodiment of the invention, method 500 further includes operation 540, for associating a signature/finger-print of the detectable composition (e.g. XRF marker), which is used for marking and object/material with object data including properties/parameters of the object/material such as identification of an entity responsible for disposal of the object/material as waste. The association data between the signature of the detectable composition/XRF-marker marking the object and the object parameters may then be stored in suitable data storage.

In order to effectively mark waste, a coding system may be used in which different relative concentrations and/or identities of marking compound may be associated with different entities responsible for disposal of the waste.

Figure 6:
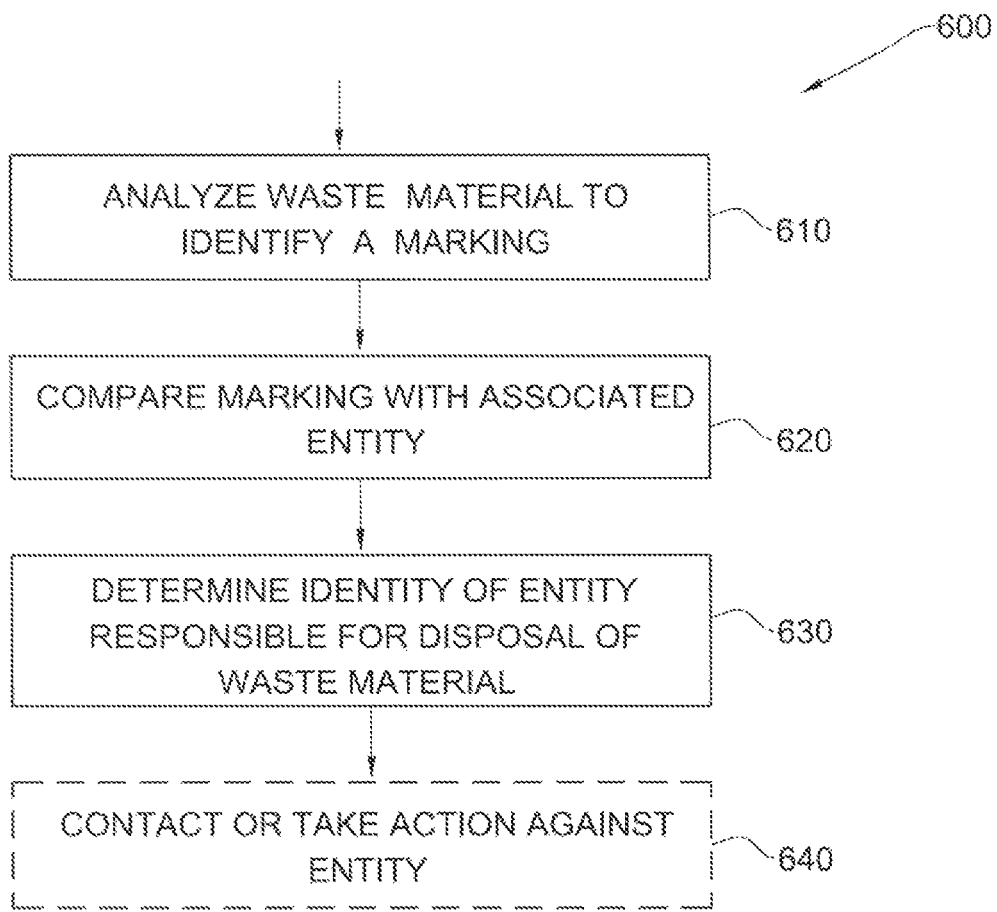
FIG. 6 shows a flow diagram depicting a process according to embodiments of the invention.

Reference is now made to FIG. 6, which shows a flow-diagram depicting a method 600, according to an embodiment of the invention, for identifying an entity responsible for disposal of a waste material.

According to an embodiment of the invention, method 600 includes operation 610 which relates to identifying/analyzing a waste material. According to embodiments of the invention, the waste material may be a solid waste material, comprising construction waste. Construction waste may comprise concrete, asphalt, metal, wood, insulation materials, drywall, glass, plastic and other associated debris. The waste material may be found dumped in illegal locations. Operation 610 may be carried out by an XRF device such as that illustrated in FIG. 4B provided in the form of an XRF marker marking spectrometer. Analyzing the waste material to identify a marking may, according to embodiments of the invention, utilize X-Ray fluorescence to identify the marking. The analysis may include bombarding the waste material with electromagnetic radiation, and analyzing the wavelength and/or intensity of fluorescence pattern emitted by the marking of the waste material. Based on the wavelength and/or intensity of the emitted fluorescence pattern, the marker may be determined to comprise a certain concentration of a specific atom associated with an identity of a marker composition. According to an embodiment of the invention, waste material is analyzed with a handheld XRF device, e.g. such as that shown in FIG. 4B.

According to an embodiment of the invention, method 600 further comprises operation 620, which relates to comparing a marking with an associated entity. Operation 620 is carried out after a fluorescence pattern (e.g. the XRF signature of the marker) is detected. The detected fluorescence pattern/XRF-signature may be indicative of specific relative concentrations of specific atoms which may correlate to concentrations of one of a plurality of markers with which waste was previously marked. The fluorescence pattern/XRF-signature emitted may be indicative of specific relative concentrations of specific atoms which may correlate to concentrations of previously applied markers. To this end, in operation 620 the reference data (described above) stored in a database may be used to compare the fluorescence pattern/XRF-signature of the detected XRF markers with the signatures/chemical-compositions of a plurality of XRF markers previously used for marking objects and stored in the data base.

According to an embodiment of the invention, method 600 further includes operation 630 which relates to determining the data of the object/waste material marked by the identified marker, for example, determining object data indicative of the identity of an entity that is responsible for disposal of the object/waste material. To this end in operation 630 the association data (described above) which is stored in the data base may be used to determine the properties/parameters of the object/material which is marked by the marker identified in 620. The property parameters of the object may include data indicative of an entity which is responsible for disposal of the object.

According to an embodiment of the invention, method 600 further includes optional operation 640 may include automatic initiation of an initiation action, against the entity responsible for disposal of the waste material. This may be for example automatic issuance of a fine to be served to the entity responsible for disposal of the waste material, and/or automatic enlisting of the entity, which is responsible for disposal of the waste, in a log/task-book for further handling by suitable personnel. To this end, as indicated above, in some cases the XRF reader device of the invention includes one or more of the following: a position locator (GPS), an optical/barcode reader, and a memory storing unique identification. Utilizing data provided by such modules, the following data parameters may be recorded when automatically logging/enlisting the disposal of the waste:

The entity which is responsible for the waste disposal—this, as well as possibly other parameters of the waste, may be determined from the association in 630;

The location of the waste disposal—this data may be obtained from the GPS/position locator of the XRF device;

The identity of the field officer who records the disposed waste—this data may be obtained by utilizing the unique identification code of the XRF device;

Possibly additional information about the waste which may be obtained from barcode information encoded on the waste objects/materials and read by the optical reader of the XRF device.

Figure 7:
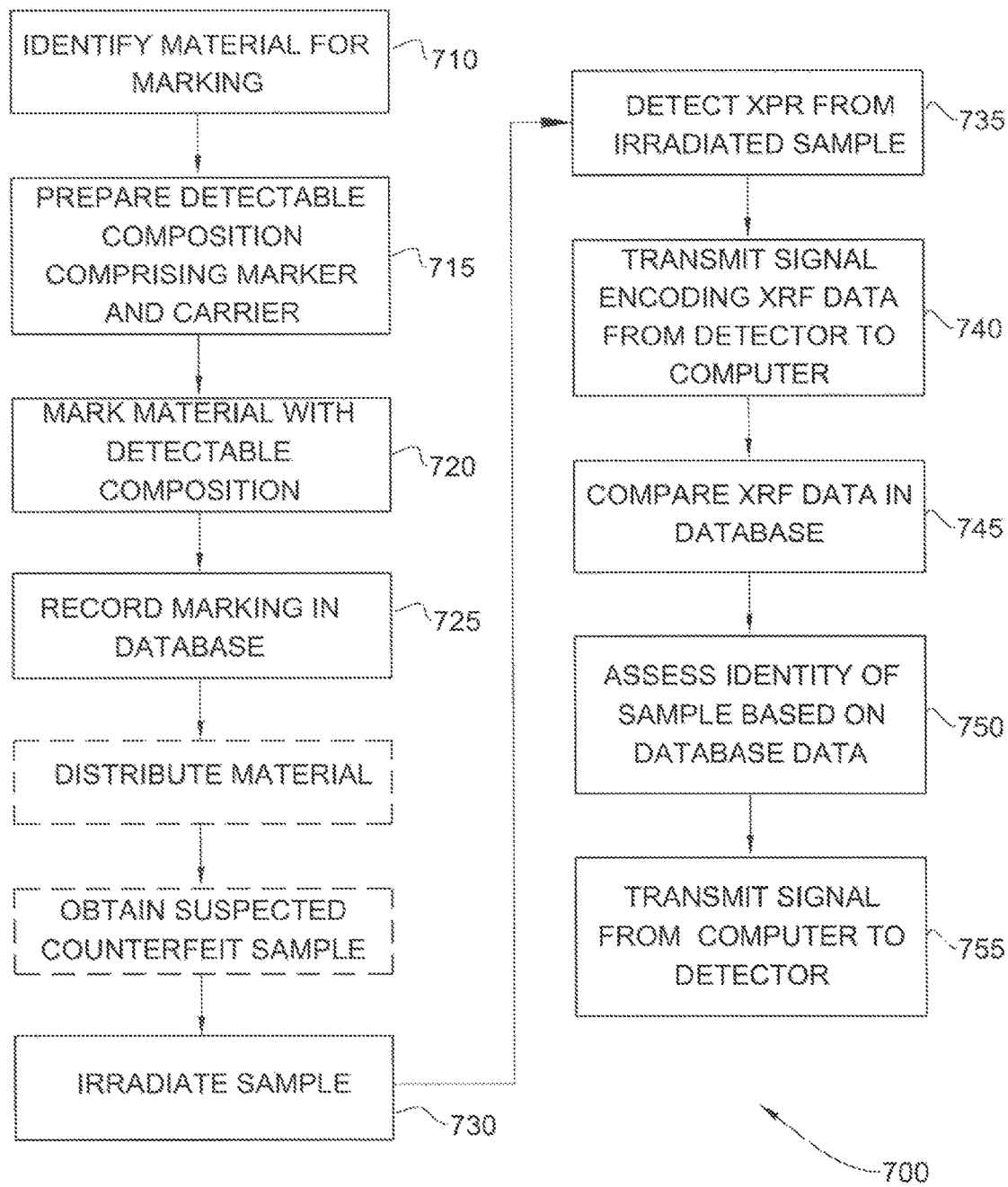
FIG. 7 shows a flow diagram depicting a process according to embodiments of the invention.

Reference is now made to FIG. 7, which shows a flow-diagram depicting a method 700 for authenticating a material according to embodiments of the invention.

Method 700 comprises operation 710, which comprises a material/object for marking. An object/material for marking may comprise any material or product in which there is concern for counterfeiting or supply chain diversion of the product. The material/object for marking may comprise a packaging which may be marked according to embodiments of the invention. The material may be selected from a group consisting of: natural gas, gemstone, coins, currency bills, identification documents, identification cards, passports, auto parts, branded goods, consumer goods, plastic, paper, adhesives, paints, pigments, nylon, cotton, synthetic fibers, metals, alloys, rubber, synthetic rubber, optic fiber, silicon, cardboard, inks, and synthetic polymer. According to an embodiment of the invention, the adhesive is selected from the group consisting of epoxy, polymeric glue and contact glue. According to an embodiment of the invention, the consumer goods are selected from the group consisting of: food, beverages, alcoholic beverages, electronics, clothing, jewelry, shoes, fashion accessories, watches, software, perfume, cosmetics, pharmaceuticals and artwork.

Method 700 further comprises operation 715, which provides an XRF marker composition comprising a marker substance and a carrier. The marker substance compound may be any of the markers described above (such as e.g.

substituted alkane and/or a halogenic compound, and/or alkyl or aryl halide, and/or an organometallic or a halogenic compound, and/or a salt comprising an atom having an atomic number comparable to lithium, or higher). According to an embodiment of the invention, the marker substance comprises an element having an atomic number of 12 (Magnesium) and above. According to an embodiment of the invention, the marker substance comprises a marker compound or marker atom. According to an embodiment of the invention, a detectable composition is prepared comprising two or more marker substances. According to an embodiment of the invention, the two or more marker substances emit XRF at different frequencies.

According to an embodiment of the invention, a marker substance is added at a concentration relative to the carrier, of between 0.1 parts per million and 100 parts per million. According to an embodiment of the invention, a marker substance is added at a concentration relative to the carrier, of between 0.5 parts per million and 30 parts per million.

According to an embodiment of the invention, a detectable composition is formed in which energy of XRF radiation, emitted when irradiating the detectable composition at a given energy, does not correspond to the energy of XRF radiation emitted when the marker substance is irradiated at the same energy. This ensures that non-marked substances will not emit "false-positive" signals and will be distinguishable from corresponding marked substances. It is also possible to use binder material whose XRF response does not interfere with the XRF signal of the marker.

According to an embodiment of the invention, the detectable composition does not interfere with the working of the marked substance. For example, if the marked substance is an adhesive, addition of the detectable composition does not alter the adhesiveness of the adhesive.

According to an embodiment of the invention, the detectable composition does not negatively impact the environment and is safe to handle and use for users of the marked material.

According to an embodiment of the invention, the energy and/or intensity of the XRF radiation emitted by a detectable composition when irradiated at a given energy is different than the energy and/or intensity of the XRF emitted by the marker substance or marker substances that the detectable composition comprises when irradiated alone, not in the presence of a carrier. The carrier and the marker may each contribute to the XRF "fingerprint" of the detectable composition relative to an unmarked substance.

Atoms of specific elements present in the marker substance, the carrier, and the marked substance or any combinations thereof, may all be detectable by XRF. When irradiated with the appropriate energy, each element may emit a variety of types of energy based on electrons reverting to various shells. Each shell, for example, a K-shell, L-shell, M-shell and N-shell, may each emit a specific amount of energy which differs for each element and each shell. A combination of reading of energy levels from a marked, irradiated substance may show, when displayed on a graph, multiple peaks corresponding to various energy levels for each element, relating to elements in any combination of marker substance, carrier and the marked substance. Methods according to embodiments of the invention attribute unique XRF fingerprints to predetermined combinations of the marker substance, carrier and the marked substance. The unique XRF fingerprints obtained from analysis of combinations of marker substance, carrier and the marked substance, may not be obtainable from analysis of the marker substance, carrier and marked substance alone.

According to an embodiment of the invention, a marker substance is mixed with a carrier. According to an embodiment of the invention, a marker substance is chemically bound to the carrier.

Method 700 further comprises operation 720, which comprises marking a material with a detectable composition.

According to an embodiment of the invention, the material is marked with a detectable composition by mixing the detectable composition with the material to form a mixture. According to an embodiment of the invention, the mixture is a uniform mixture. If the marked material is a liquid material, such as paint, the detectable composition is chosen so that it is dispersed uniformly in the liquid material and does not settle out of the liquid material over time.

According to an embodiment of the invention, the material is externally marked. According to an embodiment of the invention, the material is coated or painted with a detectable composition. According to an embodiment of the invention, a packaging of the material is marked. The material may be marked at its place of manufacture.

Method 700 further comprises operation 725, which comprises recording a marking in a database. The database may be configured to provide a unique code corresponding to a detectable composition marking. The unique code may correspond to an XRF fingerprint/signature associated with the detectable composition marking. Unique codes may be generated for each combination of marker or combination of markers. For example operation 725 may include storing in the database reference data indicative of the signature of the marking composition used for marking the object and possibly also storing association data associating properties and/or identity of the object with the signature of the marking. The coding is preferably stored in a secure database with limited access. Concentration of each marker may be varied to provide multiple options of coding. According to an embodiment of the invention, different products/objects may be marked with the same marker at concentrations which differ from each other by about 10 ppm. Methods according to embodiments of the invention are successful in distinguishing the marked objects with a confidence level of two-sigma.

The codings, and their associated fluorescence patterns may be associated with data regarding the marked material, including, but not limited to, identity of product, identity of manufacturers, batch numbers, manufacturing date, manufacturing site and/or serial numbers.

The operations 730 to 755 of method 700 described in the following are generally performed after the marked object/material is distributed (e.g. sold) and a suspected counterfeit sample is provided/found. The sample may be a sample of a material which appears similar to and/or is labeled similarly to a marked item.

Method 700 may further include operation 730, which comprises irradiating the sample. The sample may be irradiated with X-Rays or Gamma rays. Samples may be irradiated with energy of up to 40 keV.

According to an embodiment of the invention, the sample is irradiated using a handheld XRF device. According to an embodiment of the invention, the sample is irradiated by an XRF technician who does not know the identity of the detectable composition.

Before or after irradiating the sample, the operator of the handheld XRF device may input into the handheld XRF device that he requests to test authentication of a specific material. The operator may indicate, using text or a serial number associated with the material, which material is being verified. The handheld XRF device may transmit to a central computer database regarding the operator's indication of material.

According to an embodiment of the invention, the handheld XRF device may comprise a barcode reader configured to scan a barcode, QR code or other type of optically encoded data. The optically encoded data may then be transmitted to a central computer, indicating what type or manufacturer of material will be analyzed.

Optionally, method 700 may further include operation 735, which comprises detecting XRF from the irradiated sample. According to an embodiment of the invention, the detection is performed using a handheld XRF device. According to an embodiment of the invention, a silicon drift diode detector is used for the detection. According to an embodiment of the invention, XRF is detected at a range of between about 2 and 30 keV.

Optionally, method 700 may further include operation 740, which comprises transmitting a signal encoding the XRF data received from the detector to a central computer. The XRF data may include data regarding energy and/or intensity of the X-ray fluorescence of the sample. The XRF data may include data indicative of the wavelengths spectral profile of the XRF signal before and/or after filtration to remove the trend and/or periodic components therefrom. The XRF data signal may be encrypted.

Transmission of the signal from the XRF device may be performed, by way of example, through wired, wireless, telephonic or cellular communication, or any combination thereof.

Transmission from the XRF device to the central computer may include an identifier signal, unique to the XRF device to identify the XRF device for retrieval of information. The central computer may be configured to continue communication with the XRF device or to transmit information to the XRF device only upon verification of the XRF device via a unique identifier signal.

Optionally, method 700 may further include operation 745, which comprises comparing the received XRF data to data in the database. Received XRF data may be logged in a database. Logged received XRF data may be used for future analyses of future samples.

Optionally, method 700 may further include operation 750, which comprises assessing identity of a sample based on the database data. Assessing identity may be performed using a statistical analysis in which received XRF data is compared to database XRF data and a statistical comparison is performed. If a predetermined level of similarity is shown, the XRF data is considered to be from a matching sample.

Optionally, method 700 may further include operation 755, which comprises transmitting a signal from the computer to the detector device. The signal can comprise identification of data regarding the material marked, including, but not limited to, manufacturers, batch numbers, manufacturing date, manufacturing site, and serial numbers.

Alternatively, the signal transmitted may comprise an indication of a positive reading indicating a positive identification of an authentic item, or a negative reading indicating that the item is not authentic. The transmitted signal may be an indication that the sample does or does not correspond to the information inputted regarding the sample by the XRF operator.

According to an embodiment of the invention, a log of the communication between the central computer and the XRF detector may be recorded in a database.

Reference is now made to FIG. 4, which depicts a system that may be used according to embodiments of the invention for identification of materials and/or for analysis of waste and determination of its source.

Figure 8:
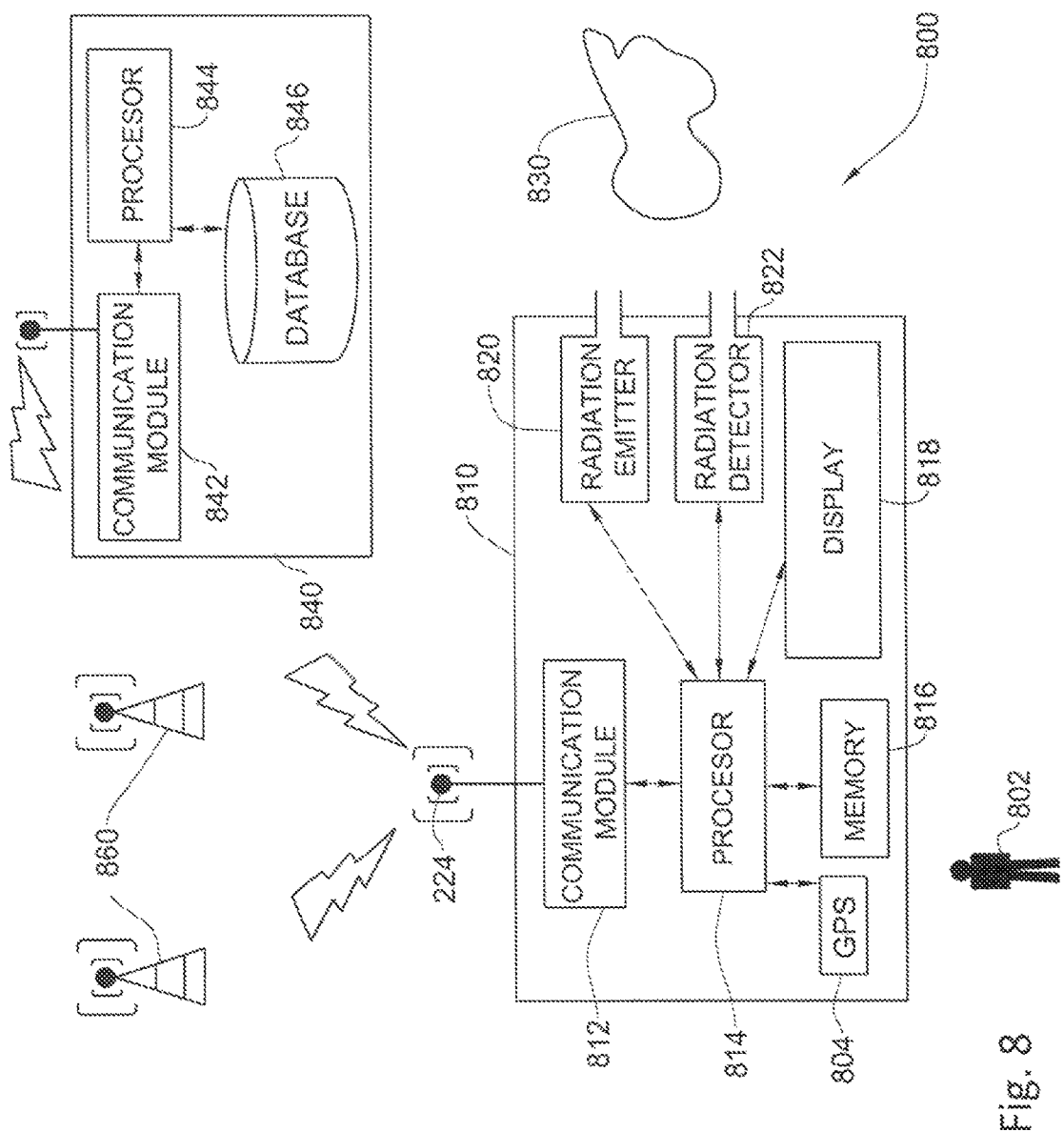
FIG. 8 depicts a system which may be used according to embodiments of the invention for analysis of material and/or analysis of waste and determination of its source.

FIG. 8 relates to a material analysis system 800 according to embodiments of the invention. Material analysis system 800 comprises a mobile XRF device/analyzer 810 capable of reading XRF signals of objects and a central computer 840 capable of receiving data indicative of the XRF signals, and/or signature thereof, and in response retrieving data/parameters indicative of objects marked by a corresponding XRF marker. At least one of the central computer 840 and the XRF device/analyzer 810 may be configured similarly to the XRF device 300 described above with reference to FIG. 3 and include an XRF-marking reading processor 310 (implemented by software and/or hardware) that can filter the wavelength spectral profile according to the technique of the invention described above (e.g. implementing method 100 and/or method 200 described above).

Mobile XRF analyzer 810 comprises a communication module 812, a processor 814, a memory 816, a display 818, a radiation emitter 820, a radiation detector 822 and an antenna 824. Central computer 840 comprises a communication module 842, a processor 844, and a database 846 storing reference and/or association data relating to the marking signatures with and respective properties of the objects marked thereby (e.g. the respective entities responsible for disposal of the object).

In some embodiments the material analysis system 800 is configured in a cloud-based configuration and/or utilize Internet based computing so that parts of processor 814, processor 844, database 846 and/or memory 816 may reside in multiple distinct geographic locations.

The Mobile XRF device/analyzer 810 may be a handheld device. In operation, operator 802 may hold a handheld mobile analyzer 810 to analyze sample/object 830 of material or waste. Upon activation of the handheld mobile analyzer 810 the processor 814, signals to radiation emitter 820 to emit radiation (e.g. X-ray radiation). Processor 814 detects a radiation fluorescence signal pattern via radiation detector 822 which is emitted from marking a composition on sample 830. Processor 814 may transmit data regarding the fluorescence signal pattern (such as fluorescence wavelength and or intensity) via communication module 812, via a data communication (e.g. via cellular network 860) to communication module 842 of the central computer 840. The processor 244 of the central computer 840 may record the received data in database 846 and/or may query/cross-reference the received data with data in database 846 to retrieve object data about the sample/object 830 (e.g. details of the object and/or identify entity responsible for its disposal) and may communicate such object data to the mobile device at which processor 814 may signal to display 818 to display a message corresponding to the object data.

In view of the above, embodiments of the invention provide convenient methods for marking and analysis of materials and of waste. An XRF technician may easily analyze materials to determine if they are counterfeited or genuine. An environmental waste technician may easily analyze illegally dumped waste using a portable, hand-held machine that may quickly and easily identify the entity responsible for illegal disposal of the waste.

Methods according to embodiments of the invention may be illustrated by the examples below:

EXAMPLE 1

The engineering department of the city of Haifa, Israel, is responsible for road works within the limits of the city. The department has offered 10 tenders (numbered 1-10) for various road construction projects in the city. All 10 tenders involve removal of large amounts of construction waste consisting of road waste. No landfills for construction waste exist in the Haifa area, and as a result, construction waste must be hauled about 100 km to the nearest landfill. The landfill charges, per 10 yard roll-off dumpster, amount to about $500. All 10 tenders are won by different contractors, designated by letters A-J.

The Engineering Department of the city of Haifa employs an environmental consultant to ensure that construction waste from the construction works in Haifa will not be illegally dumped in the Haifa vicinity. The consultant prepares detectable compositions in the form of white road paint comprising two different marker compounds, a compound comprising Li and a compound comprising Br. The asphalt road surfaces to which the detectable compositions are applied, as well as the non-marker ingredients of the road paint, are analyzed, to determine that no detectable amounts of Li or Br are present. Once the determination is made, detectable compositions are prepared according to table 1 in levels of parts per million, and are designated to specific construction sites and contractors.

TABLE 1

| Construction Site | Contractor | Li content (ppm) | Br content (ppm) |
|---|---|---|---|
| 1 | A | 10 | 10 |
| 2 | B | 50 | 10 |
| 3 | C | 100 | 10 |
| 4 | D | 10 | 50 |
| 5 | E | 50 | 50 |
| 6 | F | 100 | 50 |
| 7 | G | 0 | 100 |
| 8 | H | 10 | 100 |
| 9 | I | 50 | 100 |
| 10 | J | 100 | 100 |

The consultant prepares unique detectable compositions, according to Table 1, and applies this to road surfaces in areas which will potentially be destroyed upon starting road construction by each of the 10 contractors. The consultant applies detectable compositions at sites 1-10 before construction begins, without the knowledge of contractors of the location and composition of the marking.

Upon finding illegally disposed construction waste, the Haifa municipality may inform the consultant, who analyzes samples of the construction waste. The consultant finds, using X-Ray fluorescence, that a sample was marked with a detectable composition comprising 10 ppm of Li and 100 ppm of Br. The consultant informs Haifa municipality that the illegally disposed waste is from construction site 8, under the responsibility of contractor H. Haifa municipality may take legal action against contractor H for illegally dumping waste materials.

As illustrated in the above example, the municipality was not aware of the correlation between specific markings and contractors to which the markings corresponded. The consultant was the only entity aware of the code corresponding specific markers to corresponding contractors. This process allows control and maintenance of codes outside of the hands of municipalities. Furthermore, it allows for statewide or countrywide databases to monitor waste disposal.

Methods according to embodiments of the invention may use relatively inexpensive marking compounds to provide hundreds of thousands of possibilities of unique markings of waste, associated with an equally large number of entities responsible for the disposal of the waste.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. An X-Ray Fluorescence (XRF) device comprising:
   a radiation detector for detecting X-Ray signals arriving from an object in response to irradiation of the object by X-Ray or Gamma-Ray radiation, and providing data indicative of the detected X-Ray signals; and
   a signal reading processor in communication with said detector, the processor being adapted for receiving and processing the detected X-Ray signals to identify signatures of materials included in said object;
   wherein said processor comprises: a spectral data provider configured for determining data indicative of a wavelength spectral profile of at least a portion of the detected X-Ray signals; and a filtration module adapted for filtering said data indicative of the wavelength spectral profile and obtaining a filtered profile, said filtering being configured to suppress trend components and periodic components from said wavelength spectral profile to obtain said filtered profile, wherein said trend components and periodic components are associated with at least one of noise and clutter in the X-Ray signal portion detected by said radiation detector; said filtered profile thereby having improved signal to noise ratio (SNR) or improved signal to clutter ratio (SCR), enabling identification of spectral peaks associated with signatures of materials included in said object with improved accuracy and reliability,
   wherein said filtration module comprises a stationarity filter operative for suppressing said trend component, said stationary being adapted to carry out the following:
   a. applying moving average processing to said wavelength spectral profile or to said suppressed periodicity wavelength spectral profile to obtain a stationary profile indicative of said trend component, and
   b. differencing between the said wavelength spectral profile or said suppressed periodicity wavelength spectral profile and the stationarity profile to obtain a wavelength spectral profile with said trend component suppressed.

2. The XRF device according to claim 1 comprising an identification module configured and operable for processing said filtered profile to identify therein one or more peaks satisfying a predetermined condition and associated with XRF signatures of materials included in said object; and
   a data storage storing association data associating information indicative of a plurality of objects with marking data indicative of a plurality of XRF markers used for marking the respective objects, whereby the marking data of each respective object is indicative of XRF signatures of one or more materials of a respective XRF marker marking the object; and
   wherein said identification module identifies said object by associating the marking data of the XRF marker marking the object with the XRF signatures of materials included in the object data obtained for said object.

3. The XRF device according to claim 1 configured as a handheld XRF detection device; the XRF device comprises a communication module configured to communicate data indicative of said filtered profile to a remote processing center and to obtain from the processing center, in response, object data indicative of said object; and wherein one or more of the following:
   i. the XRF device further comprises a position locator configured to identify the position of the XRF device, and wherein said communication module is capable of communicating data indicative of said position to said processing center together with said data of the filtered profile;
   ii. the XRF device further comprises an optical reader configured to read an optical code associated with said object and wherein said communication module is capable of communicating data indicative of said optical code to said processing center together with said data of the filtered profile;
   iii. the XRF device further comprises a memory storing an identification code unique to the XRF device, and wherein the XRF device is configured to transmit the identification code to a central computer via the communication module.

4. The XRF device according to claim 1 wherein said processor is adapted for carrying out the following:
   operating said filtration module to apply said filtering to filter a plurality of wavelength spectral profiles of a plurality of portions of the X-Ray signal arriving from the object in a plurality of time frames, to suppress trend components and periodic components from said plurality of wavelength spectral profiles; and
   computing said filtered profile from data indicative of said plurality of the wavelength spectral profiles being filtered.

5. The XRF device according to claim 4 wherein computing said filtered profile comprises calculating an average profile of said plurality of the wavelength spectral profiles being filtered.

6. The XRF device according to claim 1 wherein said filtration module is adapted to apply a time series technique to the wavelength spectral profile to suppress said trend component and said periodic components and to obtain said filtered profile having improved SNR or SCR.

7. The XRF device according to claim 1 wherein said filtration module is adapted to utilize a predetermined Auto-Regressive (AR) model for carrying out said filtering.

8. The XRF device according to claim 7 wherein said predetermined Auto-Regressive (AR) model is an Auto-Regressive-Integrated-Moving-Average (ARIMA) model.

9. The XRF device according to claim 1 wherein said filtration module is adapted to utilize at least one of: Box-Jenkins processing and Seasonal-Decomposition processing, in filtering said portion of the detected X-Ray signal.

10. The XRF device according to claim 1 wherein said filtration module comprises a seasonality filter operative for suppressing said periodic component; said seasonality filter being adapted to carry out the following:
   a. applying moving average to said wavelength spectral profile obtained to obtain a smoothed wavelength spectral profile;
   b. differencing between said wavelength spectral profile and said smoothed wavelength spectral profile to thereby obtain a seasonality profile indicative of said periodic component, and smoothing said seasonality profile by computing a moving medial average thereof; and
   c. differencing between said wavelength spectral profile and said seasonality profile thereby obtaining a suppressed periodicity wavelength spectral profile with said periodic component suppressed.

11. The XRF device according to claim 1 wherein the radiation detector enables detection of an XRF marker material marking said object and having concentration in the order of 100s of ppb, and more preferably enables detection of XRF marker material and having concentration in the order of 1 ppm.

12. An X-Ray Fluorescence (XRF) device comprising a processor adapted for obtaining data indicative of a wavelength spectral profile of the X-Ray signal portion arriving from an object in response to irradiation of said object by X-Ray or Gamma-Ray radiation and detected by a radiation detector, and processing said wavelength spectral profile to identify signatures of materials included in said object;
   wherein said processor comprises a filtration module adapted for filtering said wavelength spectral profile to suppress trend components and periodic components from said wavelength spectral profile, wherein said trend components and periodic components are associated with at least one of noise and clutter in the X-Ray signal portion detected by said radiation detector; and wherein said filtration module is adapted to carrying out said filtering by utilizing one or more of the following:
   (i) a seasonality filter operative for suppressing said periodic component, whereby the seasonality filter is adapted to carry out the following:
      a. applying moving average to said wavelength spectral profile obtained to obtain a smoothed wavelength spectral profile;
      b. differencing between said wavelength spectral profile and said smoothed wavelength spectral profile to thereby obtain a seasonality profile indicative of said periodic component, and smoothing said seasonality profile by computing a moving medial average thereof; and
      c. differencing between said wavelength spectral profile and said seasonality profile thereby obtaining a suppressed periodicity wavelength spectral profile with said periodic component suppressed; and
   (ii) a stationarity filter operative for suppressing said trend component; said stationarity filter being adapted to carry out the following:
      a. applying moving average processing to said wavelength spectral profile or to said suppressed periodicity wavelength spectral profile to obtain a stationarity profile indicative of said trend component; and
      b. differencing between the said wavelength spectral profile or said suppressed periodicity wavelength spectral profile and the stationarity profile to obtain a wavelength spectral profile with said trend component suppressed
   thereby obtaining a filtered profile with improved signal to noise or signal to clutter ratio from which spectral peaks associated with signatures of materials included in said object can be identified with improved accuracy and reliability.

13. The XRF device according to claim 12 comprising a radiation detector for detecting X-Ray signals emitted from said object in response to irradiation of said object by said X-Ray or Gamma-Ray radiation, wherein said radiation detector is associated with spectrometer detection providing data indicative of said wavelength spectral profile of the detected X-Ray signal portion.

14. A method for authenticating an object marked with XRF marking, the method comprising:
filtering a wavelength spectral profile of a detected portion of an X-Ray signal arriving from an object in response to X-Ray or Gamma-Ray radiation applied to the object, said filtering being configured to suppress trend and periodic components from the wavelength spectral profile and thereby obtain a filtered profile; wherein said trend components and periodic components are associated with at least one of noise and clutter in the X-ray signal portion detected by said radiation detector, said filtered profile thereby having improved signal to noise ratio (SNR) or improved signal to clutter ratio (SCR);
identifying one or more peaks in the filtered profiled satisfying a predetermined condition thereby enabling utilizing wavelengths of said one or more peaks to identify signatures of materials included in said object, and
wherein said filtering includes one or more of the following:
i. applying seasonality filtration for suppressing said periodic component;
said seasonality filtration comprising:
a. applying moving storage to said wavelength spectral profile to obtain a smoothed wavelength spectral profile;
b. differencing between said wavelength spectral profile obtained and said smoothed wavelength spectral profile to thereby obtain a seasonality profile indicative of said periodic component, and smoothing said seasonality profile by computing a moving medial average thereof; and
c. differencing between said wavelength spectral profile and said seasonality profile thereby obtaining a periodicity free wavelength spectral profile with said periodic component suppressed; and
ii. applying stationarity filtration for suppressing said trend component, said stationarity filtration comprising:
a. applying moving average processing to said wavelength spectral profile or to said periodicity free wavelength spectral profile to obtain a stationarity profile indicative of said trend component; and
b. differencing between said wavelength spectral profile or said periodicity free wavelength spectral profile and said stationarity profile to obtain a wavelength spectral profile with said trend component suppressed.

15. The method according to claim 14 comprising one or more of the following:
irradiating said object with said radiation;
detecting a portion of an X-Ray signal arriving from an object in response to X-Ray or Gamma-Ray radiation applied to the object; and
applying spectral processing to the detected X-Ray signal to obtain data indicative of wavelength spectral profile thereof within a certain X-Ray band.

16. The method according to claim 14 comprising carrying out said filtering for wavelength spectral profiles associated with a plurality of portions of the X-Ray signal arriving from the object in a plurality of time frame portions of the X-Ray signal detected during a plurality of time frames, and obtaining said filtered profile by computing an average of a plurality of filtered spectral profiles obtained by said filtering of the plurality of portions of the X-Ray signal obtained in said plurality of time frames respectively.

17. The method according to claim 14 wherein said one or more peaks satisfying the predetermined condition include peaks indicative of X-Ray Fluorescence (XRF) response of XRF materials marking said object; and wherein the method comprising utilizing said wavelengths and possibly magnitudes of the one or more peaks to determine material data indicative of types and concentrations of materials included in said object, and utilizing said material data to authenticate said object.

18. The method according to claim 14 wherein said filtering comprises:
i. providing a predetermined Auto-Regressive-Integrated-Moving-Average (ARIMA), for filtering spectra of XRF signals;
ii. applying at least one of: Box-Jenkins processing and Seasonal-Decomposition processing to said portion of the detected X-Ray signal.

19. The method according to claim 18 (i) wherein at least one of the following:
a. Auto-Regressive orders, q and p, of said ARIMA model are respectively q=12 and p=5; and
b. Auto-Regressive weights of said ARIMA model are determined in accordance with an autocorrelation function of said wavelength spectral profile.

20. An X-Ray Fluorescence (XRF) device comprising:
a radiation detector for detecting X-Ray signals arriving from an object in response to irradiation of the object by X-Ray or Gamma-Ray radiation, and providing data indicative of the detected X-Ray signals; and
a signal reading processor in communication with said detector, the processor being adapted for receiving and processing the detected X-Ray signals to identify signatures of materials included in said object;
wherein said processor comprises: a spectral data provider configured for determining data indicative of a wavelength spectral profile of at least a portion of the detected X-Ray signals; and a filtration module adapted for filtering said data indicative of the wavelength spectral profile and obtaining a filtered profile, said filtering is configured to suppress trend components and periodic components from said wavelength spectral profile to obtain said filtered profile, wherein said trend components and periodic components are associated with at least one of noise and clutter in the X-Ray signal portion detected by said radiation detector; said filtered profile thereby having improved signal to noise ratio (SNR) or improved signal to clutter ratio (SCR), enabling identification of spectral peaks associated with signatures of materials included in said object with improved accuracy and reliability;
wherein said filtration module filtration module comprises a seasonality filter operative for suppressing said periodic component; said seasonality filter being adapted to carry out the following:
a. applying moving average to said wavelength spectral profile obtained to obtain a smoothed wavelength spectral profile;
b. differencing between said wavelength spectral profile and said smoothed wavelength spectral profile to thereby obtain a seasonality profile indicative of said periodic component, and smoothing said seasonality profile by computing a moving medial average thereof; and c. differencing between said wavelength spectral profile and said seasonality profile thereby obtaining a suppressed periodicity wavelength spectral profile with said periodic component suppressed.

21. The XRF device according to claim 20 wherein said processor is adapted for carrying out the following:

operating said filtration module to apply said filtering to filter a plurality of wavelength spectral profiles of a plurality of portions of the X-Ray signal arriving from the object in a plurality of time frames, to suppress trend components and periodic components from said plurality of wavelength spectral profiles; and computing said filtered profile from data indicative of said plurality of the wavelength spectral profiles being filtered.

22. An X-Ray Fluorescence (XRF) device comprising:

a radiation detector for detecting X-Ray signals arriving from an object in response to irradiation of the object by X-Ray or Gamma-Ray radiation, and providing data indicative of the detected X-Ray signals; and a signal reading processor in communication with said detector, the processor being adapted for receiving and processing the detected X-Ray signals to identify signatures of materials included in said object;

wherein said processor comprises: a spectral data provider configured for determining data indicative of a wavelength spectral profile of at least a portion of the detected X-Ray signals; and a filtration module adapted for filtering said data indicative of the wavelength spectral profile and obtaining a filtered profile, said filtering being configured to suppress trend components and periodic components from said wavelength spectral profile, wherein said trend components and periodic components are associated with at least one of noise and clutter in the X-Ray signal portion detected by said radiation detector; said filtered profile thereby having improved signal to noise ratio (SNR) or improved signal to clutter ratio (SCR), from which spectral peaks associated with signatures of materials included in said object can be identified with improved accuracy and reliability; and wherein said XRF device is configured as a handheld XRF detection device, and comprises a communication module configured to communicate data indicative of said filtered profile to a remote processing center and to obtain from the processing center, in response, object data indicative of said object; and wherein one or more of the following:

i. the XRF device comprises a position locator configured to identify the position of the XRF device, and wherein said communication module is capable of communicating data indicative of said position to said processing center together with said data of the filtered profile;

ii. the XRF device comprises an optical reader configured to read an optical code associated with said object and wherein said communication module is capable of communicating data indicative of said optical code to said processing center together with said data of the filtered profile;

iii. the XRF device comprises a memory storing an identification code unique to the XRF device, and wherein the XRF device is configured to transmit the identification code to a central computer via the communication module.

* * * * *